(12) United States Patent
Lau

(10) Patent No.: US 8,551,122 B2
(45) Date of Patent: Oct. 8, 2013

(54) HANDHELD SAFETY SUTURING DEVICE

(75) Inventor: William Travis Lau, Beachwood, OH (US)

(73) Assignee: Tufts Medical Center, Inc., Boston, MA (US)

( * ) Notice: Subject to any disclaimer, the term of this patent is extended or adjusted under 35 U.S.C. 154(b) by 161 days.

(21) Appl. No.: 13/055,253

(22) PCT Filed: Jul. 24, 2009

(86) PCT No.: PCT/US2009/051656
§ 371 (c)(1),
(2), (4) Date: Mar. 14, 2011

(87) PCT Pub. No.: WO2010/011900
PCT Pub. Date: Jan. 28, 2010

(65) Prior Publication Data
US 2011/0295277 A1  Dec. 1, 2011

Related U.S. Application Data

(60) Provisional application No. 61/083,192, filed on Jul. 24, 2008, provisional application No. 61/148,238, filed on Jan. 29, 2009, provisional application No. 61/179,400, filed on May 19, 2009.

(51) Int. Cl.
*A61B 17/04* (2006.01)

(52) U.S. Cl.
USPC .......................................... 606/145; 606/148

(58) Field of Classification Search
USPC ........................... 606/139, 144, 145, 148, 232
See application file for complete search history.

(56) References Cited

U.S. PATENT DOCUMENTS

| 1,037,864 | A | * | 9/1912 | Carlson et al. | 606/145 |
|---|---|---|---|---|---|
| 3,349,772 | A | * | 10/1967 | Rygg Inge H | 606/145 |
| 4,161,951 | A | * | 7/1979 | Scanlan, Jr. | 606/145 |
| 4,827,929 | A | | 5/1989 | Hodge | |
| 5,417,700 | A | | 5/1995 | Egan | |
| 5,478,344 | A | | 12/1995 | Stone et al. | |
| 5,571,090 | A | | 11/1996 | Sherts | |
| 5,628,757 | A | * | 5/1997 | Hasson | 606/148 |
| 5,645,552 | A | | 7/1997 | Sherts | |
| 5,759,188 | A | | 6/1998 | Yoon | |
| 5,814,054 | A | | 9/1998 | Kortenbach et al. | |
| 5,860,992 | A | | 1/1999 | Daniel et al. | |
| 5,891,159 | A | | 4/1999 | Sherman et al. | |
| 5,891,164 | A | | 4/1999 | Dabir et al. | |
| 5,897,563 | A | | 4/1999 | Yoon et al. | |
| 5,938,668 | A | | 8/1999 | Scirica et al. | |
| 6,077,278 | A | | 6/2000 | Mayer | |
| 7,331,970 | B2 | | 2/2008 | Almodovar | |
| 2005/0090841 | A1 | | 4/2005 | Morrison | |
| 2007/0060931 | A1 | | 3/2007 | Hamilton et al. | |
| 2009/0270886 | A1 | | 10/2009 | Bellafiore et al. | |
| 2009/0326559 | A1 | | 12/2009 | Almodovar | |

FOREIGN PATENT DOCUMENTS

WO   WO2005-084356 A2   9/2005

* cited by examiner

*Primary Examiner* — Julian W Woo
(74) *Attorney, Agent, or Firm* — Duan Wu

(57) ABSTRACT

Needle-stick injuries are associated with considerable risk of morbidity for healthcare workers and patients. The present invention of a handheld surgical suturing device allows for visualization of surgical field and better control of the suture needle with possible one-hand operation The device also provides active safety features that protect the surgeon from needle-stick injury.

18 Claims, 18 Drawing Sheets

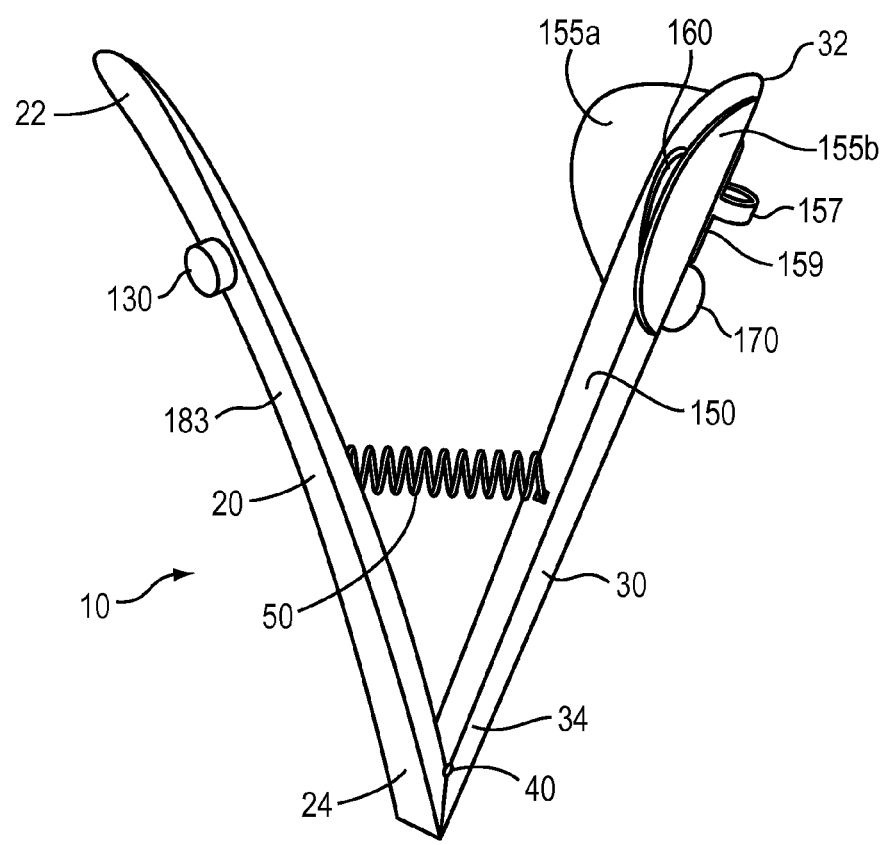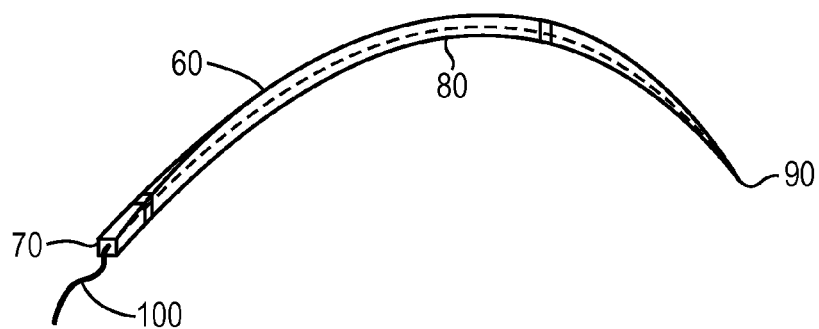
FIG. 1B

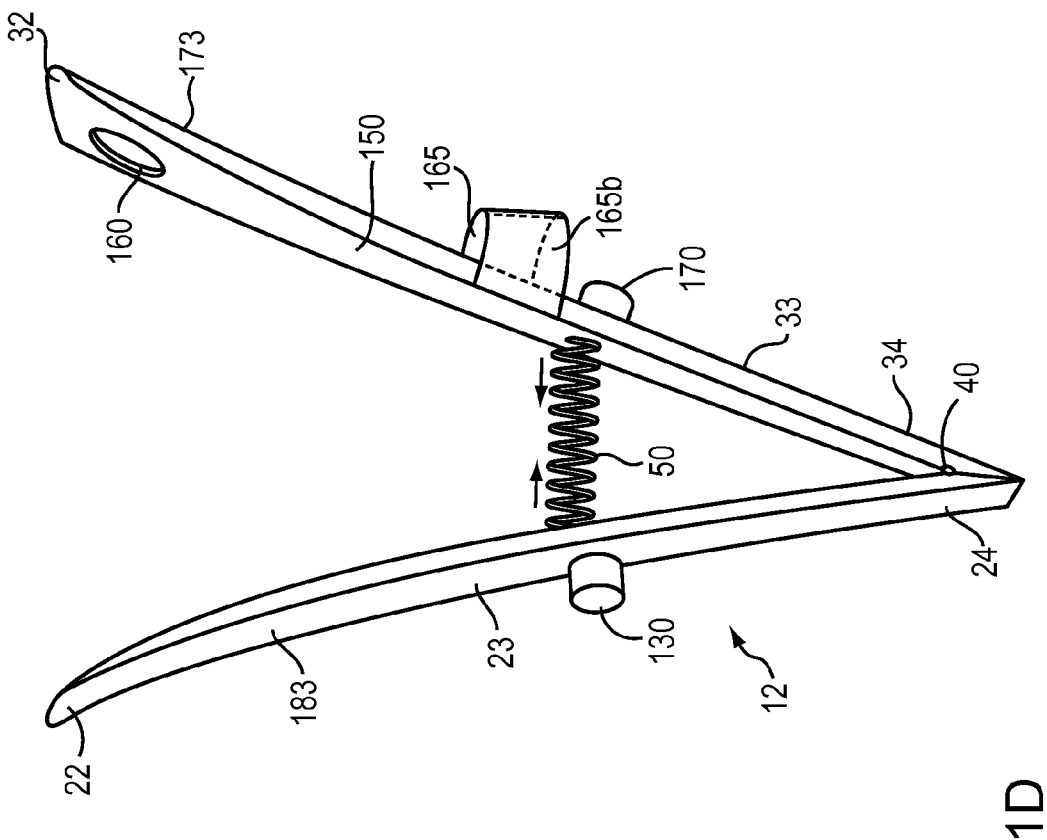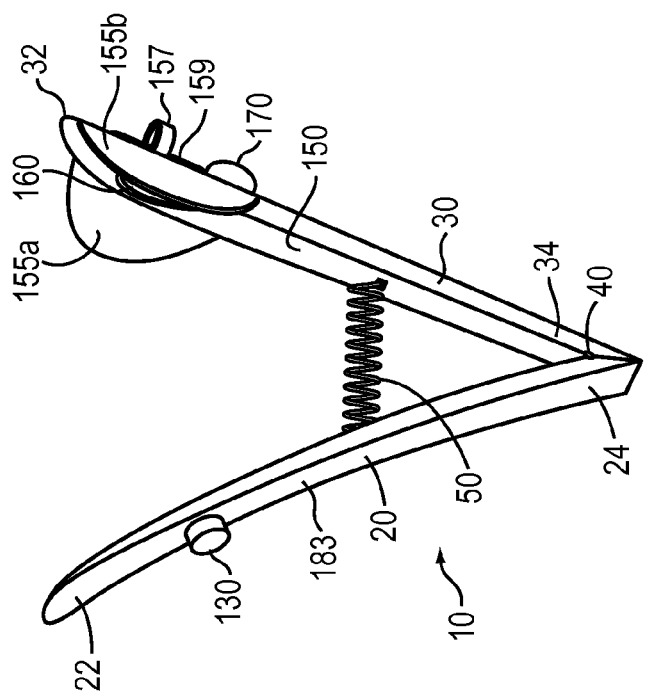
FIG. 1D

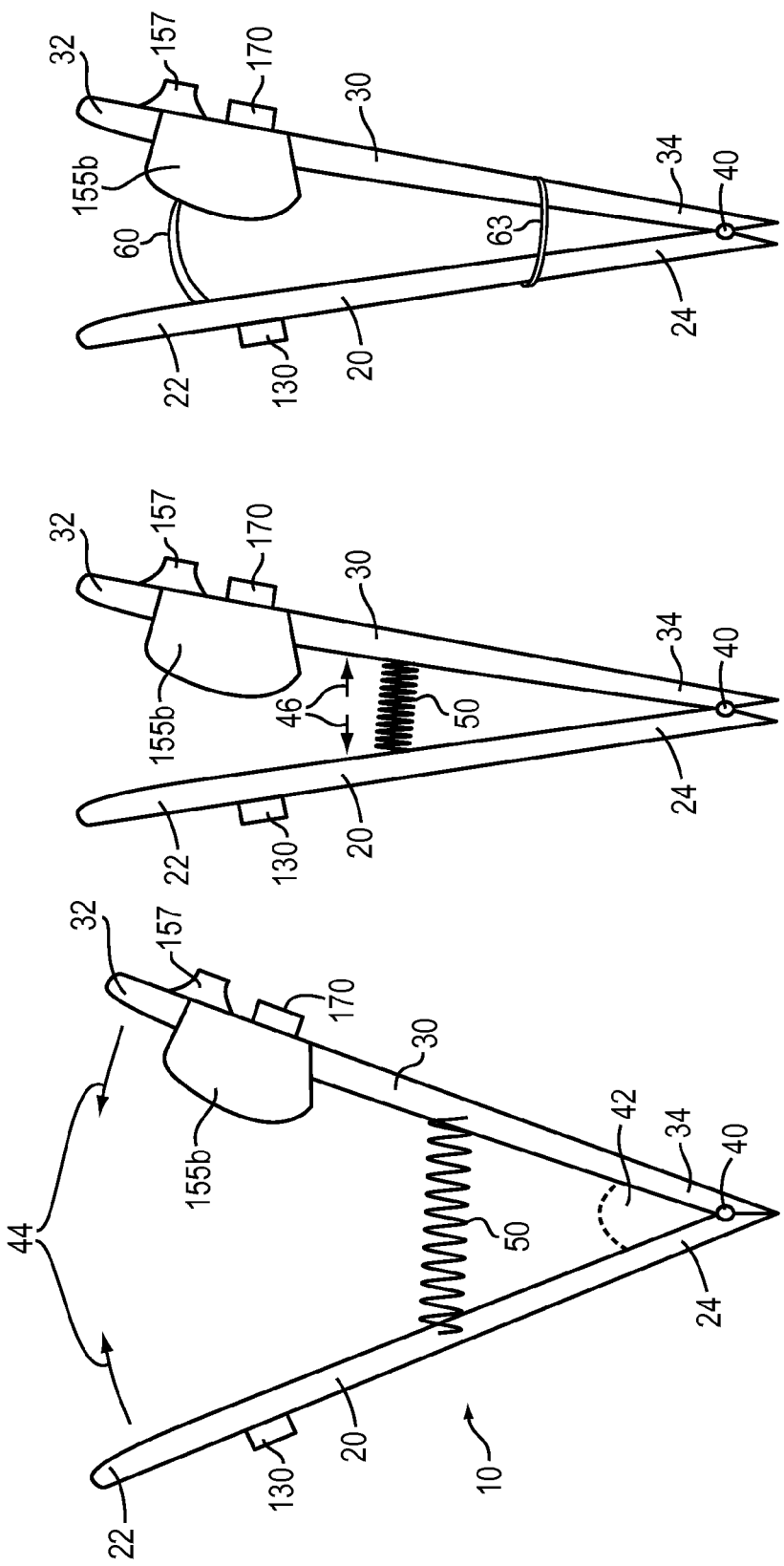

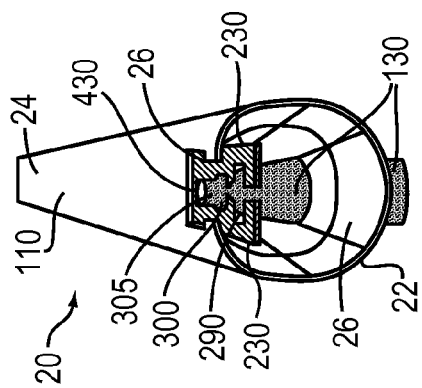
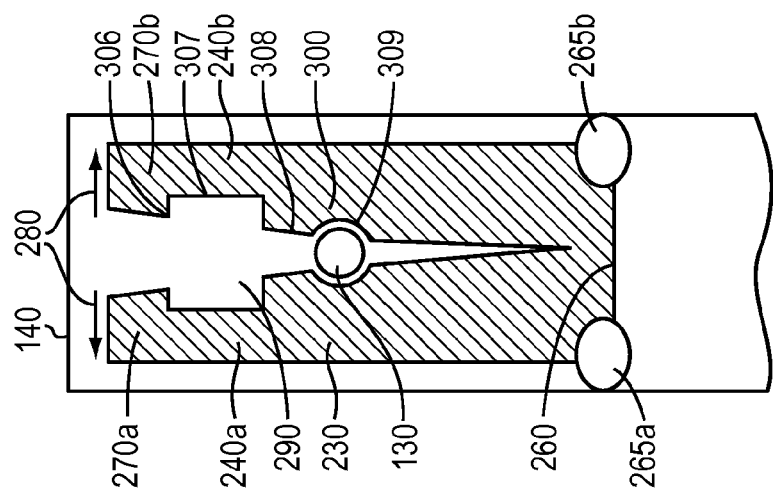
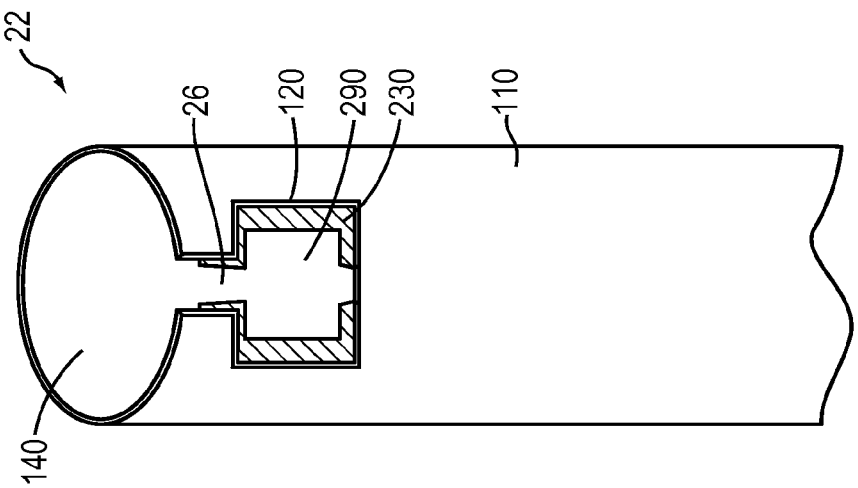

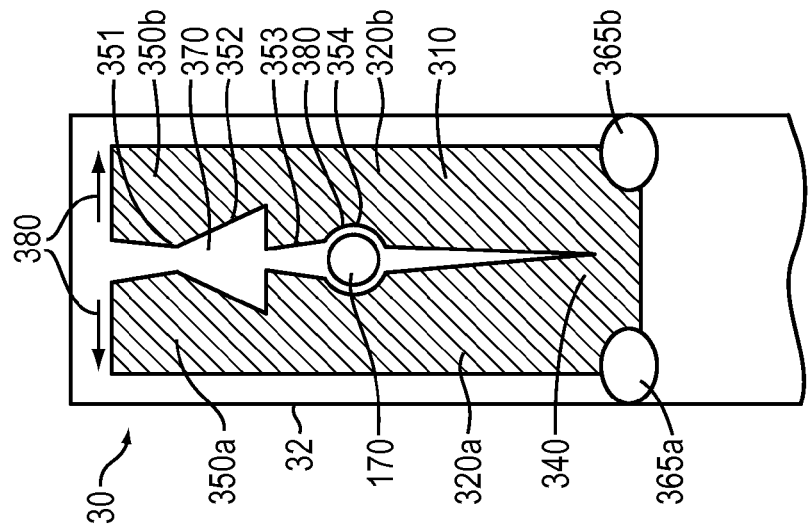
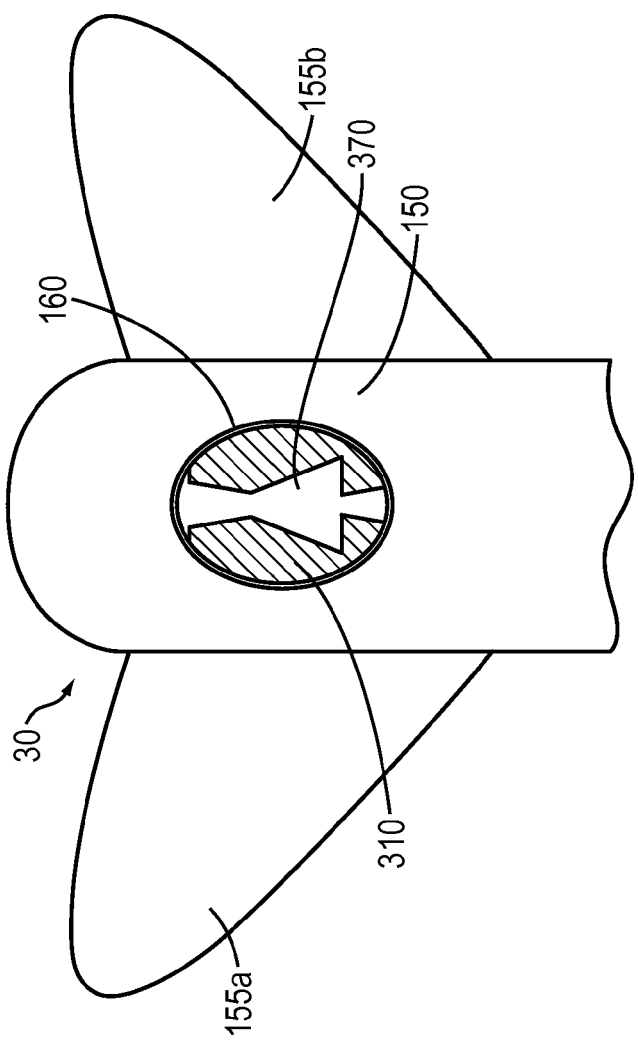
FIG. 5B
FIG. 5A

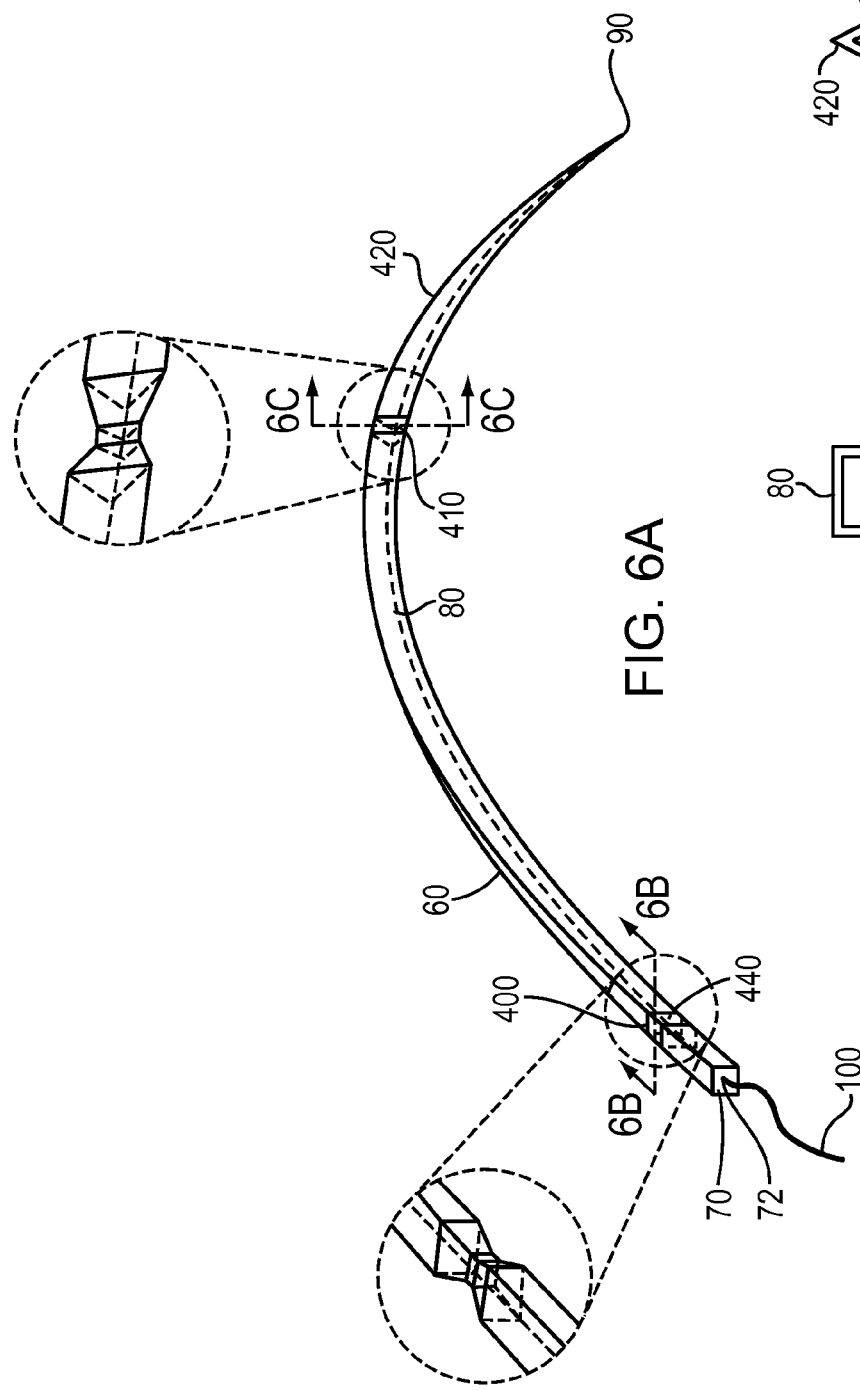

HANDHELD SAFETY SUTURING DEVICE

CROSS-REFERENCE TO RELATED APPLICATIONS

This application is based on and claims the benefit of U.S. provisional application Nos. 61/083,192 filed Jul. 24, 2008, 61/148,238 filed Jan. 29, 2009, and 61/179,400 filed May 19, 2009, the entire disclosures of which are all incorporated herein by reference.

BACKGROUND

Sutures are used in a variety of surgical applications to hold skin, internal organs, blood vessels or any other tissue together, after they have been severed by injury or surgery. Daring a standard suturing procedure, the sharp end of a curved suturing needle is passed through the tissue and the needle is pulled through manually. Manual suturing requires the use of both hands, which can block the surgical field of view. Further it involves direct handling of a sharp suturing needle usually with forceps which can result accidental slipping and needle-stick injury to the surgeon. For example, manual suturing with the straight Keith needle lends itself to even less needle control and increased risk of inadvertent needle-stick injury, especially to the inexperienced user. Needle-stick injury poses significant health risks to the surgeon because of the potential exposure to blood-borne pathogens such hepatitis virus or HIV. Lack of control of the suture needle can also lead to injury to the patient through inadvertent injury to surrounding tissues, vessels, and nerves. For example, when securing central venous access devices with a suture to the skin, poor needle control can lead to injury to the carotid artery, external jugular vein, internal jugular vein, nerves, and/or to the catheter itself.

Current designs of suturing devices that attempt to overcome these issues are extremely complex and bulky. For example, the device disclosed in 2002/0193809 describes a needle encased in a cartridge that does not permit good visualization of the surgical field. It also fails to fully protect the operator from accidental needle-stick injury.

For the forgoing reasons, there is an unmet need for devices that are simple to operate and can be manufactured inexpensively. In particular there is an unmet need for a suturing device that can be operated using one hand while also providing improved safety of operation.

SUMMARY

A handheld suturing device is disclosed that is simple in design and permits operation with one hand. Using this device, the surgeon gains greater control of the movement of a suturing needle and his surgical field is unobstructed. The device also provides added safety features to protect the operator from accidental needle stick injury. This application further discloses a suturing needle for use with the suturing device, methods of operation as well as a kit including both the suturing device and the suturing needle.

In a first aspect, a suturing device of the present invention has a driver atm with a proximal end, a distal end and a driver clasp that can reversibly secure the blunt end of a suturing needle to the driver arm. The suturing device also has a receiver arm with a proximal end, a distal end and a receiver clasp that can reversibly grasp onto the pointed end of a suturing needle. A hinge connects both proximal ends of the driver arm and the receiver arm and allows the distal ends of the driver arm and the receiver arm to converge and separate through rotation about the hinge. A spring may be disposed between the driver arm and the receiver arm and biased to separate the two arms, e.g., by less than 90 degrees.

According to one feature of the invention, the driver clasp of the suturing device includes a first driver clasp arm and a second driver clasp arm that are joined or otherwise attached to each other at their respective proximal ends. The distal ends of the arms are moveable between an open position and a closed position, in a relaxed state, the arms of the driver clasp are biased toward the closed position. Juxtaposition of the first driver clasp arm and the second driver clasp arm defines a first driver clasp aperture having a shape that largely matches a cross-section of a blunt end of the suturing needle and a second driver clasp aperture, adjacent to the first aperture, that largely matches the cross-section of a driver release button, in some embodiments, the contour of the first driver clasp aperture is non-cylindrical and has at least three sides or is rectangular.

In one embodiment, pushing the driver release button into the second driver clasp aperture pushes the first driver clasp arm and the second driver clasp arm away from each other into an open position thereby releasing any suturing needle that is previously secured by the first aperture.

According to another feature of the invention, the receiver clasp of the suturing device includes a first receiver clasp arm and a second receiver clasp arm that are joined or otherwise attached to each other at their respective proximal ends. The distal ends of the arms are moveable between an open position and a closed position. In a relaxed state, the arms of the receiver clasp are biased toward the closed position. Juxtaposition of the first receiver clasp arm and the second receiver clasp arm of the receiver clasp defines a first aperture having a contour that matches a cross-section of a pointed end of the suturing needle and a second aperture, adjacent to the first aperture that matches the cross-section of a receiver clasp button. In some embodiments, the contour of the first aperture has at least three sides or is triangular.

In one embodiment, pushing the receiver release button into the second receiver clasp aperture causes the first receiver clasp arm and the second receiver clasp arm to be pushed away from each other into an open position thereby releasing any suturing needle that is previously secured by the first receiver clasp aperture.

In one feature, the receiver arm has a shield around the aperture that is meant for the pointed needle end in order to protect the operator from accidental needle prick. In another feature, the receiver arm has a structure for the operator to pull the arm, e.g., a finger loop or hook. The shield and the finger loop/hook can be combined into one structure.

In a second aspect, a suturing needle described herein has a pointed end, a shaft and a blunt end. The pointed end can have at least three distal faces. At least one of the distal faces has at least one locking feature. The blunt end can have at least four proximal faces. At least one of the proximal faces has at least one locking feature. The locking feature may be a notch or indentation. At least one of the proximal faces may be straight. The shaft may comprise a cutting edge. The needle also has a structure for attaching a suture to it, e.g., an aperture at the blunt end of the needle.

In a third aspect, a method of suturing tissue is disclosed using the suturing device and the suturing needle described herein and preferably by a single hand entirely. Suturing starts by securing the blunt end of the suturing needle to the driver clasp within the driver arm of the suturing device of the invention. This may entail pressing the driver release button to force open the two arms of the driver clasp before inserting the blunt end of the needle into the first aperture of the driver clasp until the proximal locking feature, e.g., a notch, on the needle's blunt end is aligned with the clasp. The operator, e.g. a surgeon, releases the button at that point to lock the needle at its blunt end. Subsequently, the operator uses the driver arm to advance, i.e., to push, the pointed end of the suturing needle across the separated tissue fragments and then securing the pointed needle end to the receiver clasp within the receiver arm. Then, by pressing the driver release button, the blunt end of the suturing needle is released from the driver arm clasp. The operator can then use the receiver arm to pull the suturing needle along with the attached suturing material across the tissue fragments. Afterwards, The operator re-secures the blunt end of the suturing needle to the driver clasp of the driver arm. Pressing the receiver arm button, the operator then releases the pointed end of the suturing needle from the receiver clasp of the receiver arm. This suturing procedure results in a first suture or stitch across the tissue fragments. These steps are then repeated until the plurality of tissue fragments are sutured together by the suturing material.

According to a fourth aspect of the present invention a kit is described that includes the suturing device and the suturing needle as described herein.

It should be understood that this application is not limited to the embodiments disclosed, but instead intended to cover modifications and variations that are within the scope of those of sufficient skill in the field, and as defined by the claims.

The previously described embodiments have many advantages, including the ability to operate a suturing device with one hand operation while maintaining good manual and visual control of a suturing needle. The device further incorporates safety design features that shield the user from the sharp tip of the suturing needle.

BRIEF DESCRIPTION OF THE DRAWINGS

FIG. 1B depicts a perspective view of a suturing device as seen from slightly behind (off-center) the driver arm and a suturing needle in accordance with one embodiment.

FIG. 1D depicts a perspective view of a larger suturing device as seen from behind (off-center) the driver arm according to second embodiment together with the suturing device of FIG. 1A (shown on the left side) for comparison;

FIGS. 1E-1F show side views of the suturing device of FIGS. 1A-1B in an open (FIG. 1E) or closed (FIG. 1F) configuration.

FIG. 1G is a side view of the suturing device of FIGS. 1A-1B, with the spring removed, and both ends of a suturing needle safely locked between the two arms of the suturing device.

FIG. 4A depicts a frontal view of the inner side of a driver arm (distal end) of the suturing device shown in FIGS. 1A-1B.

FIG. 4B depicts a cross-sectional frontal view of parts depicted in FIG. 4A, illustrating a driver clasp in a driver arm of the suturing device according to one embodiment.

FIG. 4C is a perspective view of parts depicted in FIG. 4A showing a driver arm as seen from the top.

FIG. 5A depicts a frontal view of the inner side of a receiver arm (distal end) of the suturing device of FIGS. 1A-1B.

FIG. 5B depicts a cross-sectional frontal view of a receiver clasp in a receiver arm of the suturing device depicted in FIG. 5A.

FIG. 6A depicts a perspective view of a suturing needle in accordance with one embodiment of the present invention.

FIG. 6B is a cross-sectional view of the blunt end of the suturing needle of FIG. 6A taken through the line 6B-6B.

FIG. 6C is a cross-sectional view of the pointed end of a suturing needle of FIG. 6A taken through line 6C-6C.

DETAILED DESCRIPTION

The following description relates to certain illustrative embodiments of the application, and to a particular suturing device suturing needle, methodology of suturing a tissue and to a kit comprising a suturing device and a suturing needle. As will be readily apparent from the discussion, the inventive concepts described herein can also be suitably applied to other suturing devices. In addition, such terms as "top," "bottom," "lateral," "above," "below," "sagittal," "frontal," "traverse" and the like are also used in order to provide a convenient frame of reference for use with the accompanying drawings. These terms, unless stated specifically otherwise, however, are not intended to be limiting of the present invention.

The suturing device of the present invention is designed for one-hand operation, which frees up the other hand of the surgeon and opens up the surgical field of view. The freed up hand of the surgeon can now be used to better handle the wound, adjust the light source, and remove tissue, debris and blood from the suturing site. The suturing device of the present invention provides an intuitive way of moving the needle and enables the suturing of any type of tissue with increased certainty with regard to the positioning, advance, release, and recapturing of the suturing needle. And it eliminates the need for secondary tools traditionally used to assist suturing, such as needle holders, pick-up forceps, and laparoscopes. Moreover, because the suturing device of the present invention does not require the operator to directly handle the needle, it substantially reduces, if not eliminates, the risk of accidental needle sticks. The herein described suturing device is useful for the suturing of incisions or wounds in a subject including, but not limited to, humans and other mammals.

Figure 1A:
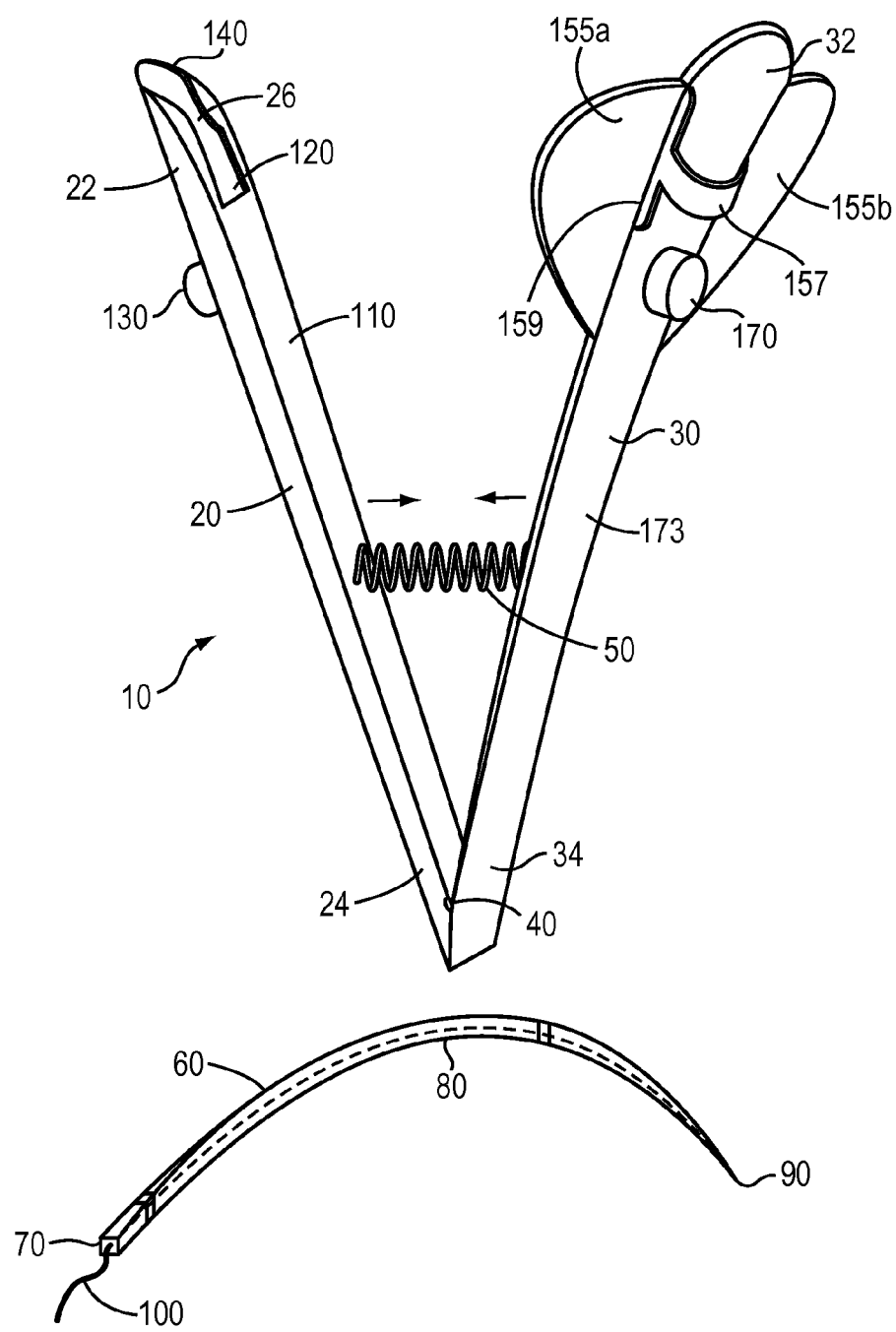
FIG. 1A depicts a perspective view of a suturing device as seen from slightly behind (off-center) the receiver arm and a suturing needle in accordance with one embodiment.

According to an embodiment, FIG. 1A and FIG. 1B illustrate external perspective views of a handheld suturing device 10. The suturing device 10 has a driver arm 20 and a receiver arm 30 that are connected at their proximal ends 24 and 34 by a hinge pin 40. A spring 50 is inserted between the arms. Compressing the distal end 22 of the driver arm 20 and the distal end 32 of the receiver arm 30 together causes them to reversibly pivot toward each other around the hinge pin 40. For ease of reference, in FIGS. 1A and 1B, a suturing needle 60 is shown that can be used with the suturing device 10. The suturing needle 60 has a blunt end 70, a shaft 80 and a pointed end 90. In this embodiment, the cross-section of the blunt end 70 is rectangularly shaped and the cross-section near the pointed end 90 is triangularly shaped. Other shapes are possible for the needle. Suturing material 100 is attached to the blunt end 70. The suturing needle is described in greater detail below in connection with FIGS. 6A-6C.

As will become apparent from this disclosure, the suturing device 10 facilitates the suturing of tissue fragments by allowing a surgeon to sequentially gasp and release either the blunt end 70 or the pointed end 90 of a suturing needle 60 using either the driver arm 20 or the receiver arm 30 as the suturing needle 60 is passed through tissue fragments during the suturing procedure.

Both the driver arm 20 and the receiver arm 30 can be, in part or in whole, straight, curved, articulated, branched, or otherwise composed of multiple segments. In one embodiment, they are not longer than a human hand, for example, from about 5 cm to about 10 cm or 20 cm. In one feature, the arms 20 and 30 are lightweight. This ensures that the suturing device 10 can be held comfortably in one hand and operated through fingertips. The driver arm 20 and the receiver arm 30 are generally of the same length and can be hollow or partially hollow or solid. For example, the distal end 22 of the driver arm 20 and the distal end 32 of the receiver arm 30 are substantially hollow because they house the suturing needle locking, mechanisms as is described in further detail below. However, one skilled in the art can readily realize other constructions for the arms 20 and 30, e.g., by having the respective needle locking mechanisms on the inside faces of the arms 20 and 20. The cross-section of the arms 20 and 30 can have any shape provided they do not interfere with the suturing procedure. For example, the cross-section of either the driver arm 20 or the receiver arm 30 can be cylindrical or largely rectangular in shape with a maximal diameter from about 0.5 cm or about 1 cm to about 3 cm or about 5 cm. The proximal end 24 of the driver arm 20 and the proximal end 34 of the receiver arm 30 are connected by a hinge pin 40 and by a compressible spring 50, inserted between the driver arm 20 and the receiver arm 30, The spring 50 is biased to separate the distal end 22 of the driver arm 20 from the distal end 32 of the receiver arm 30. In one embodiment, the spring 50 is biased to separate the two arms by less than 90, 180, or 270 degrees.

Referring now to FIG. 1A, a perspective view of the suturing device 10 is portrayed as seen by an observer located off center and behind the receiver arm 30. At the distal end 22 of the driver arm 20, the top 140 can be completely open or partially open. Below the top opening 140, on the inner face 110 at the distal cud 22 of the driver arm 20, a channel 26 connects the top opening 140 to a generally rectangularly shaped driver arm aperture 120. The blunt end 70 of a suturing needle 60 is designed to pass through this aperture 120 to gain access to the driver arm's locking mechanism. The locking mechanism (not shown) releasably secures the blunt end 70 of the suturing needle 60 to the driver arm 20 dining the suturing procedure. The top opening 140 allows any suturing material 100, attached to a secured suturing needle 60, to exit unimpeded from the interior of the driver arm 20. The driver arm aperture 120 can have any shape provided it allows sufficient space for the blunt end 70 of the suturing needle 60 to enter the distal end 22 of the driver arm 20 and to engage the driver arm's locking mechanism, for example, a clasp which is described in further detail below in connection with FIGS. 4A-4C and FIGS. 7A-7C. A driver arm release button 130 can be seen protruding from the outer face 183 (FIG. 1B) of the distal end 22 of the driver arm 20. Pressing this release button 130 enables an operator to release a suturing needle 60 from the driver arm's locking mechanism. The aperture 120 and the release button 130 can be located anywhere on the driver arm 20, including its proximal end 24 and anywhere between its distal end 22 and its proximal end 24.

Referring now to FIGS. 1A and 1B, the distal end of the receiver arm 30 of the suturing device 10 is depicted from the perspective of an observer located off center and behind the driver arm 20. On the inner side 150 of the receiver arm 30, an oval shaped receiver arm aperture 160 is visible with lateral shields 155a and 155b flanking both sides of the aperture 160. The pointed end 90 of a suturing needle 60 can be received and enclosed by passage through the receiver arm aperture 160. Further, the needle's painted end 90 can vain access to the receiver arm's locking mechanism (not shown) through this aperture 160. The locking mechanism releasably secures the pointed end 90 of the suturing needle 60 to the receiver arm 30 during the suturing procedure. For example, the receiver arm's locking mechanism can be a clasp which is described in further detail below and in connection with FIGS. 5A-5B and FIGS. 8A-8C.

Figure 2A:
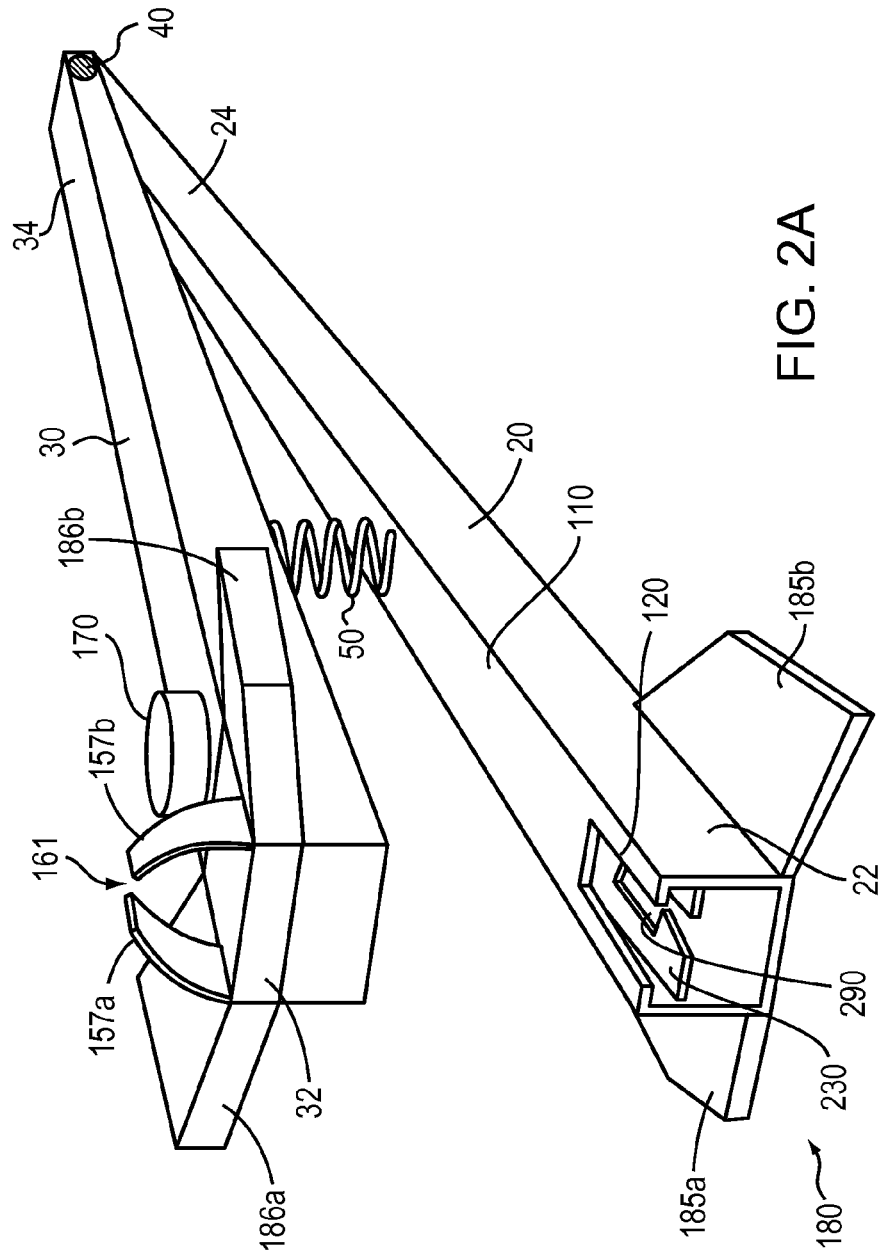
FIG. 2A shows a perspective lateral view of a suturing device in accordance with another embodiment.
Figure 2B:
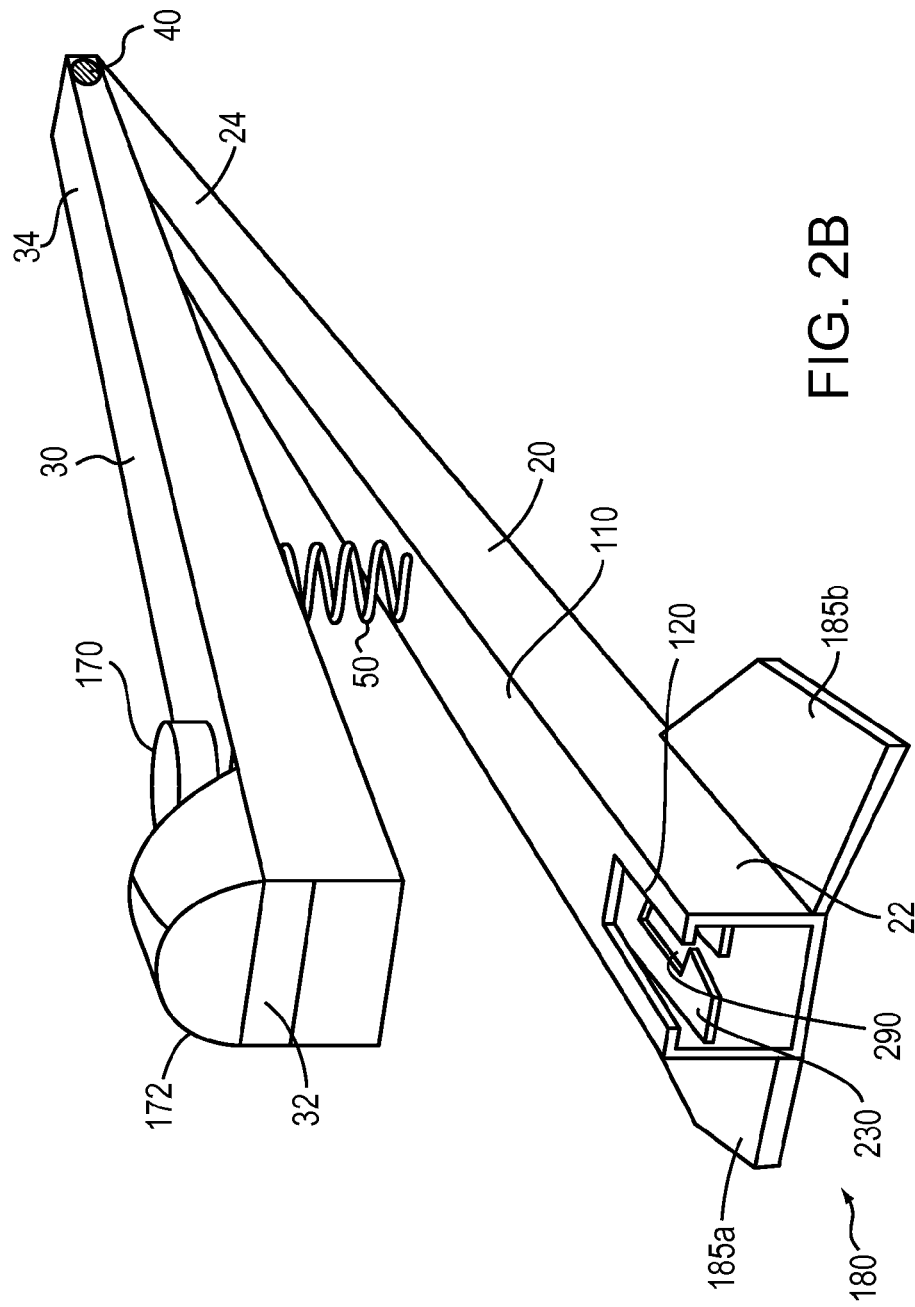
FIGS. 2B and 2C illustrate, in perspective lateral views, two embodiments with structures that enable an operator to pull the receiver arm with his finger(s).

The closed top of the receiver arm 30 and the lateral shields 155a and 155b are designed to protect the operator during; the suturing procedure from inadvertent needle sticks with the pointed end 90 of the suturing needle 60. The lateral shields 155a and 155b can have any shape provided they do not interfere with the suturing procedure and that they provide adequate protection. For example, they can be generally wing-shaped or rectangularly shaped (FIG. 2). They can project either towards the driver arm 20 (see FIG. 1B) or laterally outwards and away from the driver arm 20 (FIG. 2A), in one embodiment, additional finger rest 185a and 185b are provided on the driver arm 20 (see FIGS. 2A and 2B). In this configuration, they provide additional space for the surgeon to position his fingers and further control the operation of the suturing device 10.

At the back of the receiver arm 30 near the distal end 32 is a structure for the operator to hook one or more fingers, for pulling the receiver arm 30 during use. In the embodiment shown in FIGS. 1A and 1B, that structure is a finger loop 157 connected to the base 159 of the left shield 155a. The finger loop 157 can be a partial or full loop which the finger(s), e.g., one or more of the thumb, the index finger, the middle finger and the ring finger, can slip into. A partial loop is shown which can be easily adjusted through slight bending to accommodate fingers of different sizes. Of course, one skilled in the art readily recognizes that other configuration and structures can be provided to serve the same function and are contemplated by the invention. For example, a partial finger loop can be constructed by having two curved strips, as shown and explained in FIG. 2A and related text. Further, the shields and the finger loop can be combined into one structure; that embodiment is illustrated in FIGS. 1C, 1D, 2B and 2C and described in further detail below.

Referring back to FIGS. 1A and 1B, a receiver arm release button 170 can be seen protruding from the outer face 173 at the distal end 32 of the receiver arm 30. Pressing this button 170 enables an operator to release a suturing needle 60 from the receiver arm's locking mechanism (not shown). In one embodiment, the lateral shields 155a and 155b extend down the sides of the receiver arm 30 so as to shield the region surrounding the receiver release button 170. The aperture 160 and the release button 170 can be located anywhere on the receiver arm 30, including its proximal end 34 and anywhere between its distal end 32 and its proximal end 34.

Figure 1C:
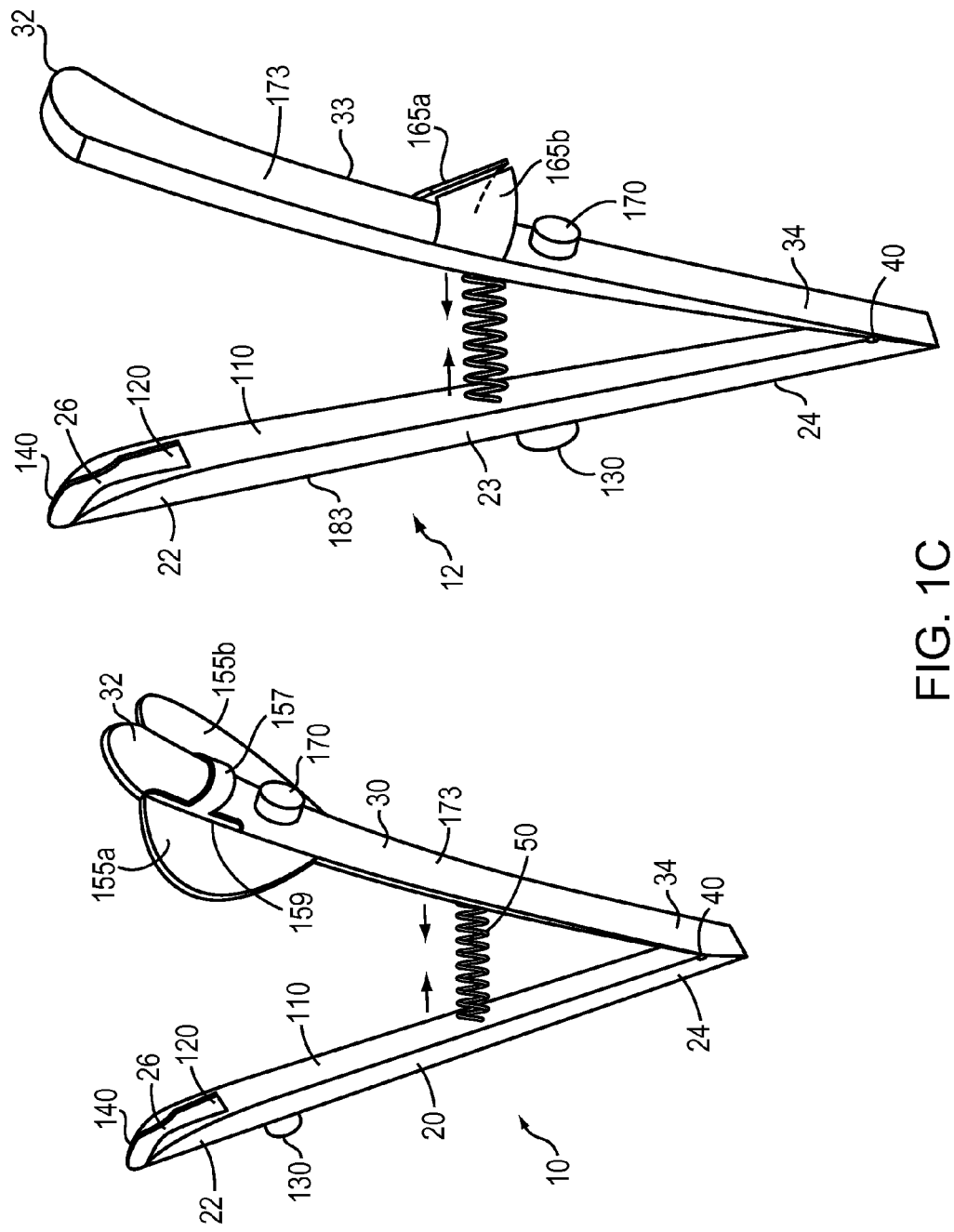
FIG. 1C depicts a perspective view of a larger suturing device as seen from behind (off-center) the receiver arm according to second embodiment together with the suturing device of FIG. 1A (shown on the left side) for comparison.

As an example of an alternative embodiment, FIG. 1C (on the right half of the figure) depicts a perspective view of an alternative suturing device 12 as seen by an observer located off center and behind its receiver arm 33. Here, the configuration of the suturing device 12 is to that of FIG. 1A except that the length of the driver arm and the receiver arm are extended as compared to the suturing device 10 of FIG. 1A (shown on the left side of FIG. 1C for comparison).

FIG. 1D (on the right half of the figure) depicts the distal end of the receiver arm 32 of the suturing device 12 of FIG. 1C from the perspective of an observer located of center and behind its driver arm 23. Here again, the configuration of the suturing device 12 is similar to that of FIG. 1B except that the length of the driver arm and the receiver arm are extended as compared to the suturing device 10 of FIG. 1B (shown on the left side of the FIG. 1D for comparison).

In FIGS. 1C and 1D, the receiver arm release button 170 can be seen protruding from the outer face 173 and is located about mid way between the distal end 32 and the proximal end 34 of the receiver arm 33. Similarly, the driver arm release button 130 can be seen protruding from the outer face 183 midway between the distal end 22 and proximal end 24 of the driver arm 23. Finger shields 165a and 165b are located just above the receiver release button 170 and also function as finger loops for the operator to pull the receiver arm 33 with his finger(s).

Locating the receiver arm release button 170 and the driver arm release button 130 at an approximately half way distance between the distal end and the proximal and of the receiver arm and driver arm respectively is for the purpose of placing those buttons within the reach of the finger(s) of an operator, thereby facilitating their operation during the suturing procedure. Depending on bow long the device's arms need to be, the location of those buttons can obviously be adjusted. For example, if an arm needs to be about thrice the length of a hand, the button on the arm should be located about a third of distance from the proximal end of the arm. With longer arms, the suturing device 12 of FIGS. 1C and 1D is particularly useful where only limited amounts of space are available for performing surgery.

FIGS. 1E-1F illustrate side views of the suturing device of FIGS. 1A-1B in an open (FIG. 1E) or closed (FIG. 1F) configuration. In this version, the proximal end 24 of the driver arm 20 and the proximal end 34 of the receiver arm 30 are connected to a cylindrical hinge pin 40. In this embodiment, the vertical axis of the pin 40 is disposed perpendicular to the vertical axis of the driver arm 20 and the receiver arm 30 and confines the movement of the driver arm 20 and the receiver arm 3 to a single plane. In this embodiment, the maximal angle of separation 42 between the driver arm 20 and the receiver arm 30 is defined by the location of the hinge pin 40 with respect to the edge of the proximal ends 24 and 34. If the hinge pin is located at the edge of the proximal ends 24 and 34 of the driver arm 20 and receiver arm 30 respectively, the driver arm 20 and the receiver arm 30 can pivot freely 360 degrees about the hinge pin 40. If the hinge pin 40 is located more distally and away from the proximal ends 24 and 34 of the driver arm 20 and receiver arm 30 respectively, as shown in FIGS. 1A-1G, the proximal ends 24 and 34 block each other from rotating freely about the hinge pin 40.

In FIG. 1E, the suturing device 10 is shown with a coiled, compression spring 50 in a relaxed state that provides a bias to separate the distal end 22 of the driver arm 20 from the distal end 32 of the receiver arm 30 by a separation angle 42. In one embodiment, the angle 42 is less than 180 degrees, 120 degrees, 90 degrees, e.g. about 60 or 45 degrees. The bias should be sufficient to separate the driver arm 20 and the receiver arm 30 in the relaxed state but should allow the operator's hand to compress the arms of the suturing device 10 toward each other with minimal effort.

In this embodiment, one end of the spring 50 is attached to the driver arm 20 between the arm's distal end 22 and proximal end 24 and the other end of the spring 50 is attached to the receiver arm 30 between the arm's distal end 32 and the proximal end 34.

FIG. 1F illustrates how movement of the driver arm 20 toward the receiver arm 30 forces the driver arm 20 and the receiver arm 30 to pivot about the hinge pin 40 in the direction 44 (see FIG. 1E). This movement results in the compression of the spring 50 that then exerts an outward tension on the driver arm 20 and the receiver arm 30 as shown by the arrows 46. The receiver arm aperture 160 is situated in such a way that, when the distal arms 22 and 32 are compressed toward each other, the receiver arm aperture 160 is positioned to be largely opposite the driver arm aperture 120. Hence, when the blunt end 70 of a suturing needle 60 is secured by the driver arm's locking mechanism, compression of the driver arm 20 toward the receiver arm 30 transports the other pointed end 90 of the engaged suturing needle 60 toward the receiver arm 30, through the receiver arm aperture 160 and into the receiver arm's locking mechanism. Alignment of the two apertures 120 and 160 depends on the curvature of the intended suturing needle 60. In one embodiment, the two apertures 120 and 160 are directly opposite each other when the two arms 20 and 30 converge.

FIG. 1G depicts an embodiment in which the spring 50 is removed from the suturing device 10 once the suturing procedure is completed. By removing and inactivating the spring 50, the outward tension 46 is eliminated. Both ends of the suturing needle 60 can then be secured and shielded within the driver arm 20 and the receiver arm 30 of the suturing device 10 prior disposal. In one embodiment, a clip 63 may be used to further secure the arms of the suturing device 10 in the closed configuration.

Still referring to FIGS. 1E and 1F, a person of ordinary skill in the art will recognize that there are many potential embodiments of the spring 50. For example, the spring 50 can be a V-shaped or U-shaped flexible metal or plastic that reversibly attaches around the outside or the ins de of the hinge 40. In another embodiment, the proximal end 24 of the driver atm 20 and the proximal end 34 of the receiver arm 30 have a cross-section that is generally U-shaped. In this configuration, the bottom of each U-shaped proximal end 24 and 34 form the outer faces of the driver arm 20 and the receiver arm 30 whereas the arms of the U-shaped proximal ends 24 and 34 project inwards. Hence, the inner face 110 at the proximal end 24 of the driver arm 20 and the inner face 150 at the proximal end 34 of the receiver arm 30 are generally open thereby allowing the arms of the U shaped proximal ends 24 and 34 to intercalate with each other. A hinge pin 40 disposed just distally from the proximal ends 24 and 34 connects the driver arm 20 to the receiver arm 30. A coiled, steel spring wrapped around the hinge pin 40 resiliently biases the driver arm 20 and the receiver arm 30 to separate. The location of the hinge pin 40 and the intercalation of the U shaped proximal ends 24 and 34, limits the pivotal movement around the hinge pin 40.

The overall dimensions of the suturing device 10 are designed to fit into one hand (see, e.g., FIGS. 1A-1B) and to be operated using the fingertips, such as the index finger and/or the middle finger and/or the ringer finger and/or little finger and/or the thumb. The relative component sizes and shapes as well as the overall size of the suturing device 10 may vary according to surgical needs (see, e.g., FIGS. 1C-1D). In one embodiment where the device 1 dimension to fit entirely into one hand, neither arm of the device is longer than about 10 cm. In another embodiment, the arms are between about 10 cm and 30 cm, for farther reach (FIGS. 1C-1D). And in some embodiments, the arms are even longer than 30 cm. The components and interior chambers may also be resized or reconfigured to accommodate surgeons with left or right-handedness. In other embodiments, the driver arm 20 and/or the receiver arm 30 may have one or more appendages or depressions or molded conformations to further facilitate the handling of the suturing device of the invention.

Referring now to FIG. 2A, an external perspective view of a handheld suturing device 180 is depicted in accordance, with another embodiment. This embodiment is similar to the suturing device 10 of FIGS. 1A-1G. However, in this version, wing-shaped structures are provided on both sides of the distal driver end 22 and the distill receiver end 32. In other words, in addition to shields 186a and 186b on the receiver arm 30, which normally receives the pointed end of the needle and poses the biggest pricking risk, structures 185a and 185b are also provided on the driver arm 20 to: (a) protect the surgeon's fingers from needle sticks when the needles are loaded incorrectly, and (b) to provide resting space for operating finger(s), e.g., the index and the middle/ring fingers. This improves the overall handling of the suturing device 180 and avoids slippage or the inadvertent activation of the release buttons 170 or 130 (viewable in FIG. 1B, for example) during the suturing procedure.

Still referring to FIG. 2A, a partial finger loop has two curved strips 157a and 157b extending from the respective bases of the two shields 186a and 186b, and meeting towards the middle—leaving a gap 161 in the middle of those two strips allows adjustment of either or both strips 157a and 157b for finger-fitting.

Referring now to FIG. 2B, in this embodiment, the functions of shielding the finger and providing a finger loop are combined into one housing, labeled as finger shield 172 here. Obviously, the finger shield 172 can be of various shapes, sizes and configurations. In a preferred embodiment, the finger shield 172 is long enough to effectively shield the finger from accidental sticks. In the particular embodiment shown, the finger shield is sized for one finger, e.g., the thumb.

Figure 2C:
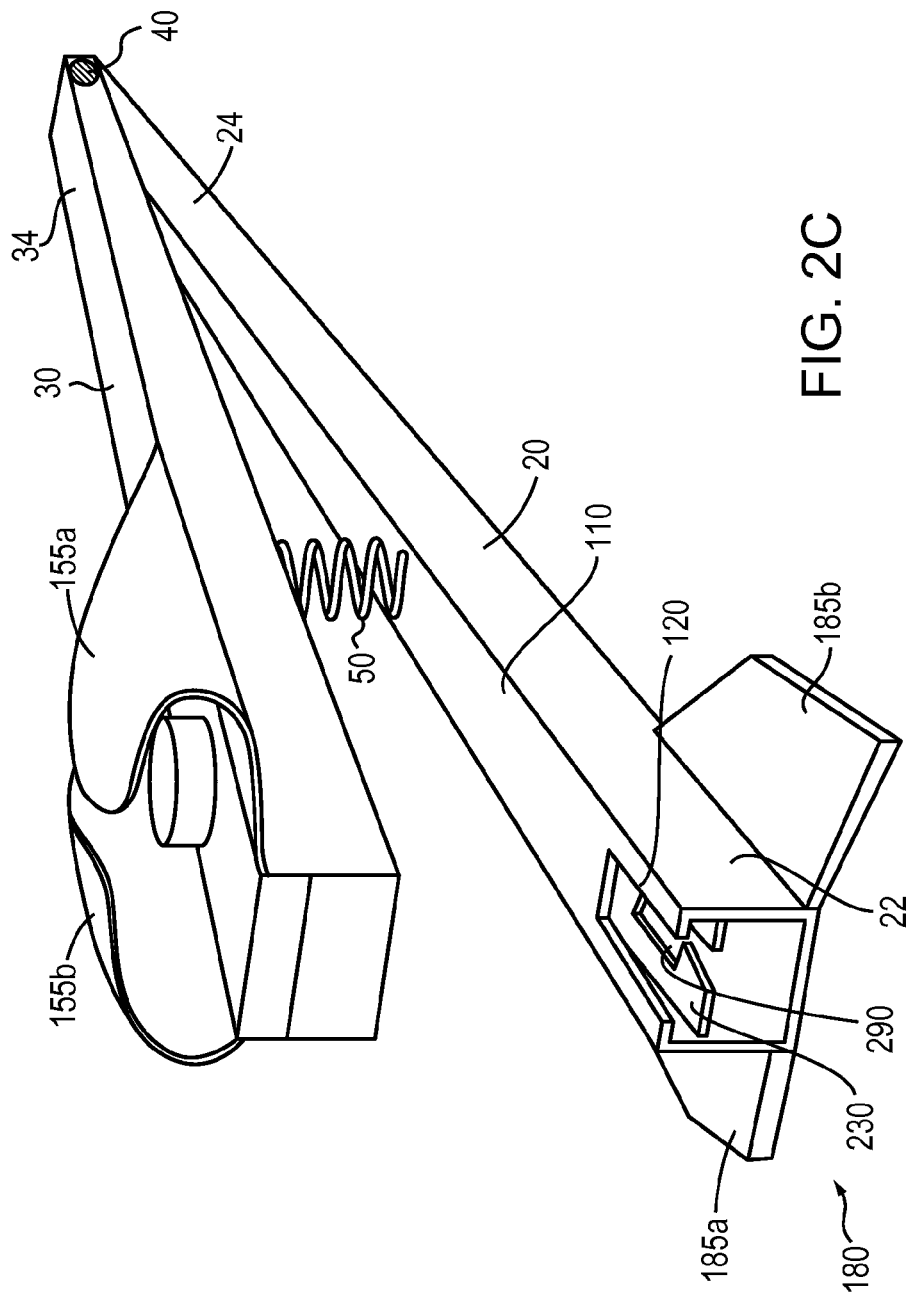

Referring now to FIG. 2C, an alternative embodiment is provided where the finger shield also functions as the finger loop or book. Here, the wing-shaped shields 155a and 155b the receiver arm 30 resemble those described in relation to FIGS. 1A and 1B except they curl up further away from the receiver arm 30 such that they form a housing that can enclose one or more fingers. The shields 155a and 155b are preferably made of materials that offer sufficient flexibility such that they can be bent to size-adjust to the operator's fingers. In this particular embodiment, the finger shields are sized and configured to fit two fingers inside, e.g., the index finger and the middle/ring finger.

The suturing device of the present invention is typically light weight. Parts of or the entire device can be made of materials suitable for single disposable use, and/or sterilizable with gamma or electron beam irradiation. The framework of the driver arm 20 and receiver arm 30 may be machined or cast using any suitable resilient, biocompatible and bio-inert material, for example, carbon fiber, nylon, another suitable polymer, a metal, or a ceramic or combinations thereof or other atraumatic, non-abrasive materials.

In one embodiment, the suturing device of the invention comprises metal components and preferably metals appropriate for surgical devices, such as stainless steel or tungsten or alloy thereof.

In another embodiment, the suturing device of the invention comprises extruded, molded, or machined thermoplastic material(s) that are known to be biocompatible with surgical applications. The suitable thermoplastic materials include, but are not limited to, poly-acrylates and methacrylates (i.e., polymethylmethacrylate, polyethyl acrylate, polybutyl methacrylate and the like); polyolefins (polyethylene, polypropylene, polybutadiene; SBS (styrene-butadiene), ethylene-propylene copolymers; SE/BS (styrene-ethylene/butadiene), polycarbonates (PC), fluorocarbon polymers (i.e., polyvinylidene fluoride (PVDF), poly-tetrafluoroethylene (PTFE), polysiloxanes, polyperfluoroethylene-propylene (FEP), various aliphatic and aromatic polymers or block copolymers, polyvinylchloride polymers, various polyesters including dacron or polyethylene terephthalate (PET) or combinations thereof.

In another embodiment, the suturing device of the invention comprises a high-strength technical ceramic, such as aluminum oxide, zirconium oxide or silicon nitride. Ceramic materials are lightweight, of high strength and are non allergic. Particularly suitable as a ceramic material is zirconium dioxide, a mixed oxide of zirconium dioxide and aluminum oxide, a silicon or nitride ceramic. Using injection mold techniques that are well known in the art, components of the suturing device 10 can be fabricated in one piece from the ceramic material which has been mixed with a polymer component. Thereafter, the binder is removed from the finished product in the presence of nitrogen and nitric acid.

Embodiments intended for repeated use must be sterilized between uses, so materials that will tolerate sterilizing agents, solvents, or autoclave temperatures are preferred.

Figure 3:
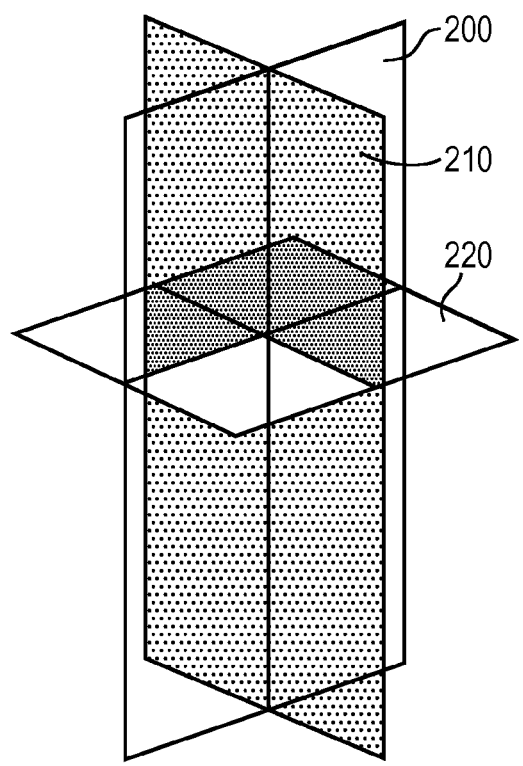
FIG. 3 illustrates the relationship between frontal, sagittal and traverse planes as described throughout the present application.

With the foregoing description of the external features of a suturing device, sectional views of the interior of the driver arm 20 and the receiver arm 30 are now described with respect to a frontal plane, a sagittal plane and a traverse plane. The relationship between these planes of view is depicted in FIG. 3. Specifically, the frontal plane 200 divides an object into front and back portions. The sagittal plane 210, which is perpendicular to the frontal plane 200, divides an object into a left half and a right half. The traverse plane 220, which is perpendicular to the frontal plane 200 and dies sagittal plane 210, divides an object into top and bottom portions.

Referring now to FIG. 4A, a side view of the inner face 110 of the distal end 22 of the driver arm 20 is shown. A driver clasp 230, which functions as a locking mechanism for a cooperating suture needle (not shown), can be seen through the driver arm aperture 120. This view therefore illustrates how the driver clasp 230 is accessible to a blunt end 70 of a suturing needle 60 passing through the driver arm aperture 120.

Referring now to FIG. 4B, a frontal view of the distal end 22 of the driver arm 20 is presented with a driver clasp 230 having a first driver clasp arm 240a and a second driver clasp arm 240b that are joined at a proximal end 260. The driver clasp 230 is secured to the internal wall of the driver arm by brackets 265a and 265b. Other means of fastening or securing the driver clasp 230 to the driver arm 20 can be used as well provided they do not impede on the locking mechanism. The function of the driver clasp 230 is to lock onto and subsequently release the blunt end 70 of the suturing needle 60 during the suturing procedure. The distal ends 270a and 270b of the clasp arms 240a and 240b are biased to fold towards each other, but, if force is applied, they are able to reversibly pivot away from each other in the direction 280. The contour of the inner edge of the first clasp arm 240a is a mirror image of the contour of the inner edge of the second clasp arm 240b. The inner edge of each clasp arm has a contour that includes, for example, from top to bottom, a first protrusion 306, a first depression 307, a second protrusion 308 and a second depression 309. In one embodiment, the first depression 307 has straight sides and the second depression 309 has curved sides. Juxtaposition of the inner edge of the first clasp arm 240a with the inner edge of the second clasp arm 240b generally defines a first driver clasp aperture 290 and a second driver clasp aperture 300. In one embodiment, the first driver clasp aperture 290 is largely rectangular in shape whereas the second driver clasp aperture 300 is largely circular in shape.

The first driver clasp aperture 290 can have any shape provided it matches the cross-section of the blunt end 70 of the suturing needle being used. It should be dimensioned to receive the tapered rectangular blunt end 70 of the suturing needle 60 and prevent the suturing needle 60 from rotating about its own axis, in one embodiment, the diameter of the tapered blunt end 70, optionally, is substantially smaller than the diameter of the needle shaft 80. Hence, by pushing, the tapered rectangular blunt end 70 into the first driver clasp aperture 290, the distal ends 270a and 270b of the clasp arms 240a and 240b are forced further apart in the direction 280. The bias of the clasp arms 240a and 240b to fold back toward each other results in the driver arm clasp 230 gripping onto the blunt end 70 of the suturing needle 60. In one embodiment of the locking mechanism, the edges of driver clasp aperture 290 align with and insert into the one or more indentations near the blunt end 70 thereby securing the blunt end 70 to the driver arm 20.

The second driver clasp aperture 300 can also have any shape provided it matches the cross-sectional shape attic tapered end of a driver arm release button 130. For example, the end of the driver arm release button 130 can be conical in shape (see also FIG. 4C). Pushing the driver arm button 130 through the second driver clasp aperture 300 forces the driver clasp arms 240a and 240b even further apart to counter the bias of the driver clasp 230 on the blunt end 70 of the suturing needle 60 and to release any suturing needle 60 that is previously secured by the first driver clasp aperture 290 to the driver clasp 230.

FIG. 4C illustrates a partial perspective view of the distal end 22 of the driver arm 20 from the perspective of an observer looking down through the open top 140. Along the inner face 110, the open top 140 is connected to the driver arm aperture 120 by a connecting channel 26. Within the hollow interior cavity, the driver clasp arms 240a and 240b define a first driver clasp aperture 290 that aligns with the driver arm aperture 120. The driver release button 130 on the outer face 183 of the driver arm 20 can be seen to traverse the outer wall 25 of the driver arm 20 into the internal cavity 28 where it is inserted into the second driver clasp aperture 300. The small conical end 305 of the driver release button 130 is opposed by a compression spring 430 connected to the inside wall of the inner face 110 of the driver arm 20. The spring 430 is biased to push the driver release button 130 out of the first driver clasp aperture 290.

In one embodiment, the driver clasp 230 is constructed with a strong spring force biased to clasp the two driver clasp arms 240a and 240b. In that embodiment, the suturing device can be used with even needles with entirely smooth body surfaces, i.e., without any indentation or special locking features, which include most of the conventional, currently off-the-shelf suture needles. In that case, the operator inserts the needle's blunt end into the driver clasp aperture 290, maybe by pressing the driver arm release button 130 to keep the clasp open, until the needle's blunt end reaches the desired depth (e.g., the back of the arm), and then simply let go of the release button and allow the spring force to lock the clasp tightly around the needle shaft. Along the same time, in other optional features, the clasp may have a textured surface or some adhesive coating where it contacts the needle shaft to strengthen the clasp's griping power in order to secure and lock the needle end.

Referring now to FIG. 5A, a perspective view of the inner face 150 at the distal end 32 of the receiving arm 30 is depicted. The receiver clasp 310, which functions as a locking mechanism for a cooperating needle (not shown), can be seen through the receiver arm aperture 160. Unlike with the driver arm 20, the top of the receiver arm 30 is closed. This vantage point illustrates how a triangularly shaped shaft 80 near the pointed end 90 of the suturing needle 60 can pass through a receiver arm aperture 160 and be inserted into a largely triangularly shaped first receiver clasp aperture 370. Shields 155a and 155b, attached laterally to the receiver arm aperture 160, protect the operator from inadvertent needle sticks.

Referring now to FIG. 5B, a frontal view of the distal end 32 of the receiver arm 30 is depicted with a receiver clasp 310 having a first receiver clasp arm 320a and a second receiver clasp arm 320b both joined at their proximal end 340. Brackets 365a and 365b attach the receiver clasp 310 to the internal wall of the receiver arm 30. Other means of fastening or securing the receiver clasp 310 to the receiver arm 30 can be used as well provided they do not impede on the locking mechanism. The function of the receiver clasp 310 is to lock onto and subsequently release the pointed end 90 of the suturing needle 60 from the receiver arm 30 during the suturing procedure. The mechanism is similar to that used by the driver clasp 230. The distal ends 350a and 350b of the receiver clasp arms 320a and 320b are likewise biased to fold towards each other, but, if force is applied, they are able to reversibly pivot away from each other in the direction 360. Again, as with the driver clasp 230, the inner edge of the first receiver clasp arm 320a is a mirror image of the inner edge of the second receiver clasp arm 320b and includes, from top to bottom, a protrusion 351, a first depression 352, a second protrusion 353 followed by a second depression 354. In one embodiment, the first depression 352 has straight sides and the second depression 354 has curved sides. Juxtaposition of the inner edge of the first receiver clasp arm 320a with the inner edge of the second receiver clasp arm 320b defines a first receiver clasp aperture 370 and a second receiver clasp aperture 380. In one embodiment, the first receiver clasp aperture 370 is largely triangular in shape and the second receiver clasp aperture 380 is largely circular in shape. The bias of the clasp arms 320a and 320b to fold back toward each other results in the receiver arm clasp 310 gripping onto the pointed end 90 of the suturing needle 60. The edges of receiver clasp aperture 370 align with and insert into the one or more indentations near the pointed end 90 thereby securing the pointed end 90 to the receiver arm 30.

The driver clasp 230 or the receiver clasp 310 can made of any suitable material such as a thin sheet of metal or stress resilient plastic. In one embodiment, the inner edges of the clasps are thin enough to insert themselves into one or more indentations near the ends of a suturing needle 60.

The first receiver clasp aperture 370 can have any shape provided it matches the cross-sectional shape of the shaft 80 near the pointed end 90 of the suturing needle 60. In one embodiment, it is dimensioned to receive the triangular shaft 80 near the pointed end 90 of the suturing needle 60. The insertion of the triangular shaft 80 into the first receiver clasp aperture 370 prevents the suturing needle 60 from rotating about its own axis.

The second receiver clasp aperture 380 can also have any shape provided it matches the cross-sectional shape of the tapered end of a receiver arm release button 170. For example, the end of the receiver arm release button 170 can be conical in shape. Pushing the receiver arm button 170 through the second receiver clasp aperture 380 forces the receiver clasp arms 320a and 320b even further apart to counter the bias of the receiver clasp 310 on the shaft 80 near the pointed end 90 of the suturing needle 60 and to release any suturing needle 60 that is previously secured by the first receiver clasp aperture 370 to the receiver clasp 310.

Similar to the driver clasp 230, the receiver clasp 310 can be used with entirely smooth needles if the spring force biasing the two receiver clasp arms 320a and 320b strong, and/or the clasp 230 is equipped with a texture surface or some adhesive coating where it contacts the needle shaft.

Referring now to FIGS. 6A-6C, a suturing needle 60 that can be used with the suturing device 10 of the present application is described. FIG. 6A shows a suturing needle 60 with a curved shape comprising a non-penetrating, rectangular blunt end 70, a needle shaft 80 and a sharp, penetrating pointed end 90. Suturing material 100 is attached to the blunt end 70, e.g., through an aperture 72, in one embodiment, one or more blunt end (or proximal) indentations 400 on the surface of the needle 60 are located near the blunt end 70 and one or more pointed end (or distal) indentations 410 on the surface of the needle 60 are located near the pointed end 90. Indentations may be around the entire or part of the circumference of the needle. In a particular embodiment, the blunt end indentations 400 are on opposites faces of the rectangular cross-section 90 of the needle shaft 80 near the blunt end 70.

The blunt end 70 may be tapered (not shown) such that the diameter at the blunt end 70 is smaller than the diameter of the needle shaft 80 near the blunt end 70. That configuration facilitates the insertion of the blunt end 70 into the driver clasp aperture 290 within the driver arm 20. In one embodiment, as depicted in FIG. 6B, a proximal section of the needle shaft 80, viewed in cross-section along the line 6B-6B near the blunt end 70, is rectangular in shape. As depicted in FIG. 6C, a distal section of the needle shaft 80, viewed in cross-section along the line 6C-6C near the pointed end 90, is triangular in shape. Non-circular needle shafts 80 have the advantage that they prevent the suturing needle 60 from rotating about its axis once it is secured by the suturing device 10. However, the cross-sections of the needle shaft 80 near the blunt end 70 or near the pointed end 90 may have any shape and still fall within the intended scope of the application. In one embodiment, the cross-section of the needle shaft 80 near the blunt end 70 has at least four faces whereas the cross-section of the needle shaft 80 near the pointed end 90 has at least three faces.

Still referring to FIGS. 6A-6C, a person of ordinary skill in the art will recognize that many different types of needle locking mechanisms may be used to secure an end of a suturing needle 60 to a suturing device 10. A locking feature may be located anywhere near an end of a suturing needle 60. It can have any configuration provided it allows a suturing needle 60 to be secured, preferably reversible, to the suturing device of the present invention and that it does not interfere with the passage of the suturing needle 60 through a tissue. In one embodiment, a needle-locking feature is located on at least one facee or on opposite faces near an end of the suturing needle 60. Each end of a suturing needle 60 may have different needle locking features. In one embodiment, a needle-locking feature may comprise one or more machined indentations, notches, apertures or depressions or protrusions or other appendages engineered at the ends of a suturing needle 60, in a preferred embodiment, a needle-locking feature is an indentation with a narrow trough-like structure that is etched onto the outside surface near one of the ends of a suturing needle 60. For example, the bottom 440 of the indentation 400 or 410 can be square or U-shaped or V-shaped or any other shape provided it permits a clasp to insert itself into and lock onto the indentation. Indentations may have a depth of about 0.5, about 1 mm, about 1.5 mm, or about 2 mm and a width of about 0.5 min, about 1 mm, about 1.5 mm, or about 2 mm depending on the size of the suturing needle 60. Indentations 400 and 410 are located at an appropriate distance from the end of the suturing needle 60 to allow a clasp of a suturing device 10 to latch onto an indentation within the confines of the driver arm or receiver arm.

In the illustrated embodiment, the indentation can span the entire or part of one, two, three or four faces of the needle shaft depending on where it is located. If the indentation spans at least an entire lateral face of the needle body, it resembles a notch when viewed from side. The indentation can also involve less than an entire lateral face, or even just constitute a pointed dent or aperture as long as it cooperates with a corresponding feature on the suturing device to facilitate locking, preferably reversible, of the needle. The indentation can be on the inside or the outside, or the lateral sides of the curvature (i.e., the arch) of the needle 60.

The needle-locking mechanism does not have to rely on structure alone, it can also rely upon or at least involve other properties, such as the tackiness of the material at a certain section near a needle's end. Furthermore, the locking feature on the needle can be a structure completely separable from either the needle, an adhesive or magnetic strip that can be affixed to an end of the needle. Separate locking features allow the use of existing, off-the shelf needles including those with cylindrical or non-cylindrical bodies.

The suturing needle 60 shown in FIGS. 6A-6C may be fabricated from any corrosion-resistant metal such as stainless steel alloys that have desired characteristics with respect to biocompatibility, strength, and the ability to take a sharp end author point when ground and polished. Generally, the needle can be fabricated from a material such as series 300 stainless steel alloy, series 400 stainless steel alloy, or non-ferrous alloy, e.g., MP35N alloy and the like.

The suturing needle 60 of the present application may mimic the contour of any suturing needle known in the art. In one version, a suturing needle 60 may have, for example, the contour of any of the suturing needles manufactured by Ethicon, Inc, a subsidiary of Johnson and Johnson. For example, it may be a round-bodied needle (such as the Taperpoint needle, Taperpoint Plus needle, VIVI-Black needle, Ethiguard Blunt Point needle, Blunt point needle, CC needle or Tapercut needle) or it may be a cutting needle (such as the Reverse Cutting needle or Trocar point needle). In another version, a suturing needle 60 of the present application may have any curvature, including, but not limited to, a ¼ circle, a ⅜ circle, a ½ circle, a ⅝ circle J shape, a compound curve or it may be substantially straight. In a preferred embodiment, a suturing needle 60 is a curved 2-0 silk suture reverse cutting needle having a triangularly shaped pointed end 90, a needle shaft 80 and rectangular shaped blunt end 70. The cutting edge 420 disposed at the outside curvature of the suturing needle 60 (see FIG. 6) facilitates the penetration and cutting of tough skin.

A cross-section of the needle shaft 80 can have any shape or multiple shapes at different locations, including, but not limited to, a circular, rectangular or triangular shape. In one embodiment, the needle shaft 80 refers to the body of a reverse cutting suturing needle that has a triangular cross-section near its pointed end 90. In this embodiment, the apex cutting edge 420 is located on the outside of the needle curvature. The triangular shape improves the overall strength of the needle and increases its resistance to bending. It also prevents rotation of the suturing needle about its own axis once it is secured to the suturing device 10.

The suturing material 100 attached to the blunt end 70 of a suturing needle 60 may be any sterile, biocompatible, strong, non-toxic, hypoallergenic and flexible material suitable for suturing skin, internal organs, blood vessels and any other tissue together, after they have been severed by injury or surgery. The suturing material 100 may be absorbable or non-absorbable depending on its intended use and may be treated with one or more additives, for example, one or more antibiotics to prevent bacterial wound infection. Absorbable suture materials are bioresorbable typically within 10 days to a few weeks. Examples of absorbable suture materials include, but are not limited to, specially prepared beef and sheep intestine (either untreated (plain gut), tanned with chromium salts to increase their persistence in the body (chromic gut), or heat-treated to give more rapid absorption (fast gut)) or various braided or monofilament synthetic polymer fibers such as various blends of polyglycolic acid, lactic acid or caprolactone. Commerically available absorbable suture materials are marketed, for example, under the brand names Biovek® (Dynek Pty. Ltd.), Vicryl PLUS® or Panacryl® (Ethicon, Inc. a Johnson & Johnson company), Visorb® (CP Medical), Polysorb® and Dexon® (Syneture). Non-absorbable suturing materials are made of materials which are not metabolized, and are therefore used either on skin wound closure or other wounds that require a greater time to heal and close. Non-absorbable sutures are typically made of processed silk, artificial fibers, like polypropylene, polyester or nylon that may or may not have coatings to enhance their performance characteristics. One example of a non-absorbable suture material is Ethibond®, manufactured by Ethicon, Inc., a Johnson & Johnson company. The surgeon will select the length, diameter, and characteristics of the suture to suit a particular application.

Figure 7A:
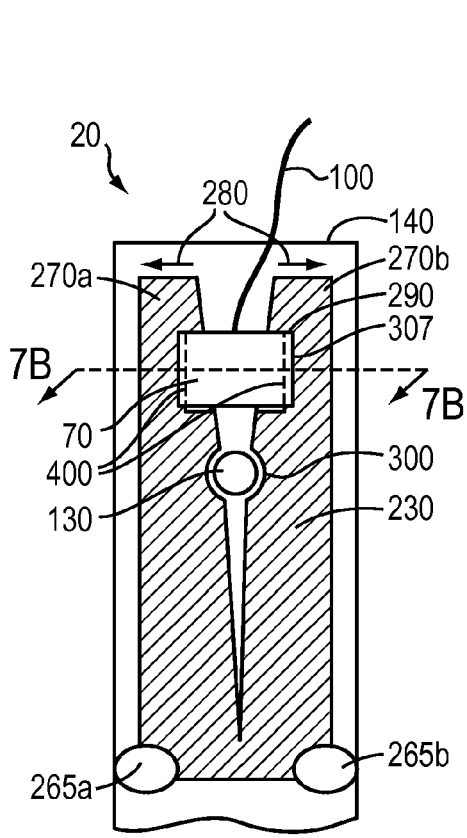
FIG. 7A depicts a cross-sectional frontal view of the driver clasp of FIGS. 4A-4C with the blunt end of the suturing needle of FIG. 6A engaged in the driver clasp.
Figure 7B:
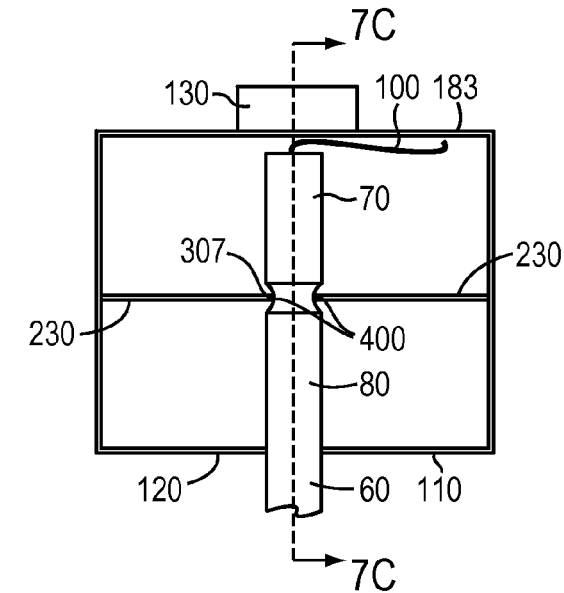
FIG. 7B is a cross-sectional view of a traverse plane of the driver clasp of FIG. 7A taken through line 7B-7B.
Figure 7C:
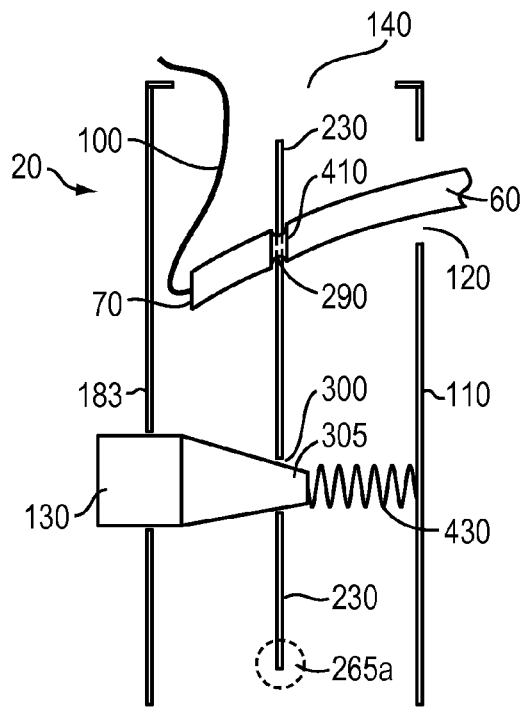
FIG. 7C is a cross-sectional view of a sagittal plane of the driver clasp of FIG. 7A inside the distal end of a driver arm of a suturing, device of FIGS. 1A-1E taken along the line 7C-7C.

FIGS. 7A-7C illustrate how the blunt end 70 of a suturing needle 60 can be reversibly secured to the driver arm 20 of the suturing device of the present invention.

Referring specifically to FIG. 7A, a frontal cross-sectional view of the driver arm 20 of FIG. 4B is shown with the blunt end 70 of a suturing needle 60 secured by the driver clasp 230. In its relaxed state, the width of the first driver clasp aperture 290 is slightly greater than the width of the tapered blunt end 70 of a suturing needle 60. Insertion of the blunt end 70 into the driver clasp aperture 290 forces the distal driver clasp arms 270a and 270b of the driver clasp 230 to move apart from each other in the direction 280 until the edges around the first depression 307 of the driver clasp aperture 290 encounter the indentation 400 near the needle's blunt end 70 at which point the two arms snap back and lock in the suturing needle 60. This locking mechanism also prevents the suturing needle 60 from rotating about its axis, thereby giving the surgeon greater control over the secured suturing needle 60. In this embodiment, the suturing material 100 can exit through the top 140 of the driver arm 20. Below the first driver arm aperture 290, the driver arm release button 130 can be pressed into the second circular driver arm aperture 300 to force apart the arms of the driver clasp 230.

In FIG. 7B, a traverse cross-sectional view through the plane 7B-7B is shown from the vantage point of an observer looking down at the top 140 of the distal arm of the driver arm 20. From this perspective, the inner face 110 of the driver arm 20 is on top. The driver release button 130 can be seen protruding from the outer face 183 further down the driver arm 20. The driver clasp 230 secures the suturing needle 60 by engaging the edges around the first depression 307 (FIG. 7A) of the driver clasp aperture 290 against the proximal (blunt-end) indentation 400 in the suturing needle 60. A portion of the needle shaft 80 passes through the driver arm aperture 120 into the inner face 110 of the driver arm 20. The blunt end 70 of the suturing needle is seen with the attached suturing material 100.

Referring now to FIG. 7C, a sagittal cross-sectional view through the plane 7C-7C is shown from the vantage point of an observer looking laterally at the distal arm 20. The top of the driver arm 140 is at the top and the inner face 110 of the driver arm 20 is on the right. From this perspective, the secured suturing needle 60 projects out through the driver arm aperture 120. The driver arm release button 130, a conical push-button type bit, extends outwards from the opposite face 183 of the driver arm 20. The end of the conical bit 305 with the smaller diameter is oriented towards the inner face 110 of the driver arm 20 and is opposed by a small stainless steel compression spring 430. Pressing the conical release button 130 through the second driver clasp aperture 300 toward the inner face 110 exerts an opening force on the distal arms 270a and 270b of the driver clasp 230 that opens up the distal arms 270a and 270b thereby releasing the suture needle 60 previously secured by the first driver arm aperture 290.

Figure 8A:
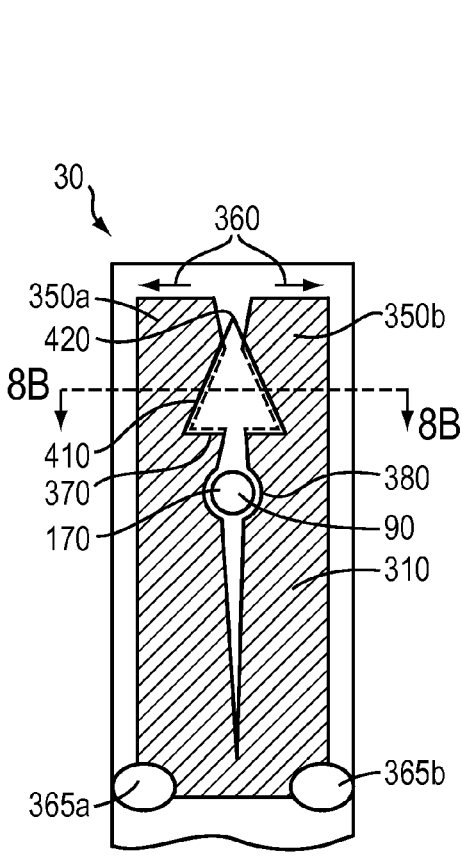
FIG. 8A depicts a cross-sectional frontal view of the receiver clasp of FIGS. 5A-5B with the pointed end of the suturing needle of FIG. 6A engaged in the receiver clasp.
Figure 8B:
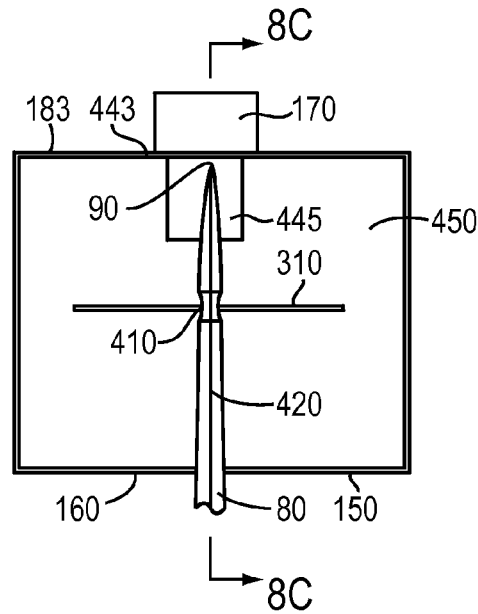
FIG. 8B is a cross-sectional view of a traverse plane a the receiver clasp of FIG. 5A taken through line 8B-8B.
Figure 8C:
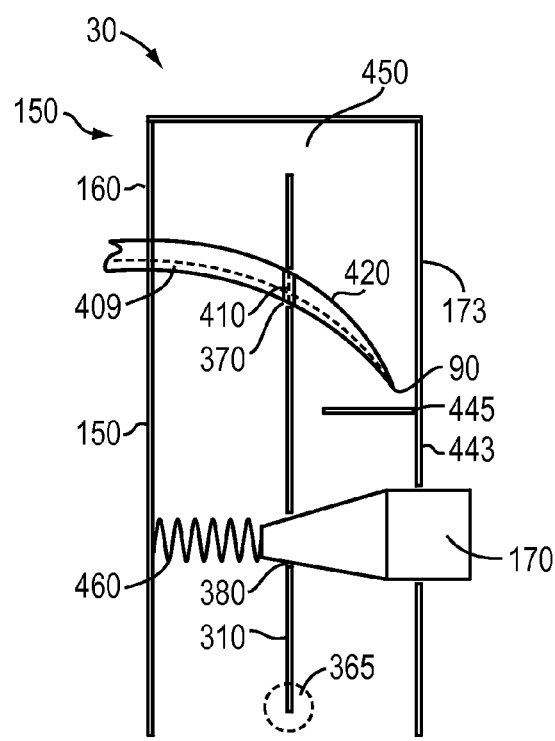
FIG. 8C is a cross-sectional view an sagittal plane of the receiver clasp of FIG. 8A inside the distal end of a receiver arm of a suturing device of FIGS. 1A-1E taken along the line 8C-8C.

FIGS. 8A-8C illustrate how the pointed end 90 of a suturing needle 60 is reversibly secured to the receiver arm 30 of a suturing device 10 of the present invention.

Referring to FIG. 8A, a frontal cross-sectional view of the receiver arm 30 is shown with the pointed end 90 of a suturing needle 60 inserted into the triangular receiver clasp aperture 370. In its relaxed state, the dimension of the first receiver clasp aperture 370 is slightly larger than the cross-sectional shape of the shaft 80 near the pointed end 90 of a suturing needle 60. In much the same way as the locking mechanism of the driver arm 20, insertion of the pointed end 90 into the first receiver clasp aperture 370 forces the distal receiver clasp arms 350a and 350b of the receiver clasp 370 to move apart from each other in the direction 360 until they encounter the indentation 410 at which point the two arms snap back and lock in the suturing needle 60. This locking mechanism prevents the suturing needle 60 from rotating about its axis. Below the first receiver arm aperture 370, the second circular receiver arm aperture 380 is occupied by an end of receiver arm release button 170.

In FIG. 8B, a traverse cross-sectional view through the plane 8B-8B is shown from the vantage point of an observer looking down at the top of the distal arm of the receiver arm 30. The top of the distal end of the receiver arm 30 is cut away to show the receiving compartment 450. From this perspective, the inner face 150 of the receiver arm 30 is on the bottom. The receiver release button 170 can be seen projecting out from the outer face 173 of the receiver arm 30. The receiver clasp 310 is inserted into the distal (pointed-end) indentations 410 near the pointed end 90 of the suturing needle 60. Part of the needle shaft 80 passes through the receiver arm aperture 160 and into the inner face 150 of the receiver arm 30. A stopper 445 protrudes from the inner surface 443 of the outer face 173 of the receiver arm 30. The stopper 445 prevents the advancement of the pointed end 90 of the suturing needle 60 beyond the confines of the receiver compartment 450. In one embodiment, the stopper 445 may be solid such as a plastic or a softer material such as rubber or a combination of a plastic extension cushioned by a coating of a rubber material.

FIG. 8C depicts a sagittal cross-sectional view through the plane 8C-8C as seen from the vantage point of an observer looking laterally at the distal arm of the receiver arm 30. The top of the receiver arm 30 is on the top and the inner face 150 of the receiver arm 30 is on the left. From this perspective, the secured suturing needle 60 protrudes out through the receiver arm aperture 160 of the inner face 150 of the receiver arm 30. Further advancement of the pointed end 90 of the suturing needle is blocked by the stopper 445. Below, the receiver arm release button 170, a conical push-button type bit, extends outwards from the outer face 173 of the receiver arm 30. The end of the conical bit 447 with the smaller diameter is oriented towards the inner face 150 of the receiver arm 30 and is opposed by a small stainless steel compression spring 460. Pressing the conical release button 170 through the second receiver clasp aperture 380 toward the inner face 150 exerts an opening force on the receiver clasp arms 320a and 320b of the receiver clasp 310. This causes the distill receiver clasp arms 350a and 350b to open up thereby releasing any suture needle 60 that is previously secured in the first receiver arm aperture 370.

With the aforementioned detailed structural description of a suturing device 10 and a suturing needle 60, a method of suturing an incision wound is now described.

Referring to FIGS. 9A-9D, a suturing device 10 is shown being held in a surgeon's left hand 455 and operated with the fingertips, e.g. the index finger 460, the middle finger 465, and the thumb 475 in accordance with one embodiment of the present application. For clarity, the surgeon's hand is shown without a glove. The suturing device 10 is retained by a pincer movement between the index finger 460 and the middle finger 465 pressing on the lateral shields 155a and 155b at the distal end 32 of the receiver arm 30 and the thumb 475 pressing on the outer face at the distal end 22 of the driver arm 20. The shields 155a and 155b in this case curve away from the receiver arm 30 and double as finger hooks. Obviously, there are alternative ways to handle the suturing device 10, e.g., having the thumb on the receiver arm and index and middle/ring finger on the driver arm.

Referring specifically to the posture depicted in FIGS. 9A-9D, application of pressure by the index finger 460 and the middle finger 465 toward the thumb 475 results in the receiver arm 30 pivoting about the hinge 468 toward the driver arm 20. In this embodiment, a spring, located within the hinge 468, is concealed from the view. As described above, in its relaxed state, the spring biases the driver arm 20 and the receiver arm 30 to stay separate at their distal ends 22 and 32.

Figure 9A:
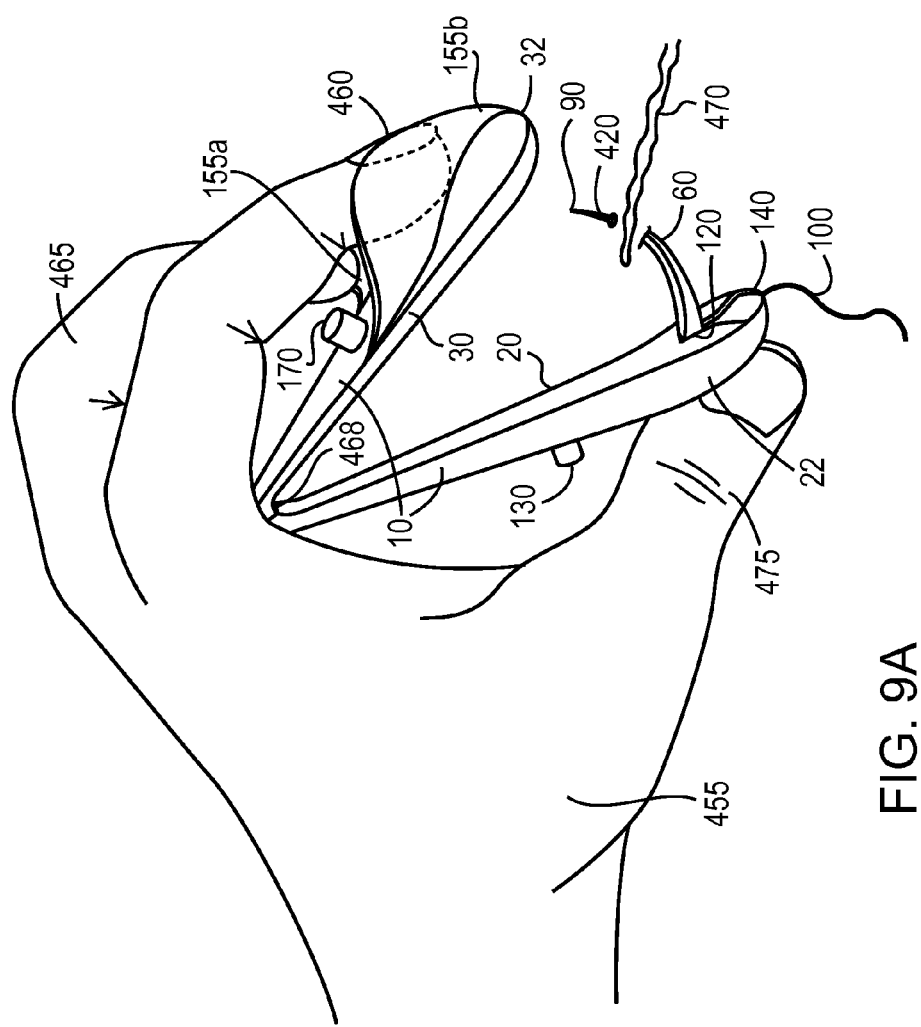
FIGS. 9A-9D illustrate sequential steps of suturing an incision wound using a suturing device and a suturing needle of the present application.

In FIG. 9A, a handheld suturing device 10 is depicted with the blunt end 70 of a suturing needle 60 secured by the driver arm's locking; mechanism within the distal end 22 of the driver arm 20. Suturing; material 100 can be seen exiting through the top 140 of the driver arm 20. With the aid of its cutting edge 420, the pointed end 90 of the suturing needle 60 is pushed across the incision wound 470 using the leverage of the driver arm 20 at stitch point 480 and exits from a corresponding stitch point 480 on the other side of the incision wound 470.

Figure 9B:
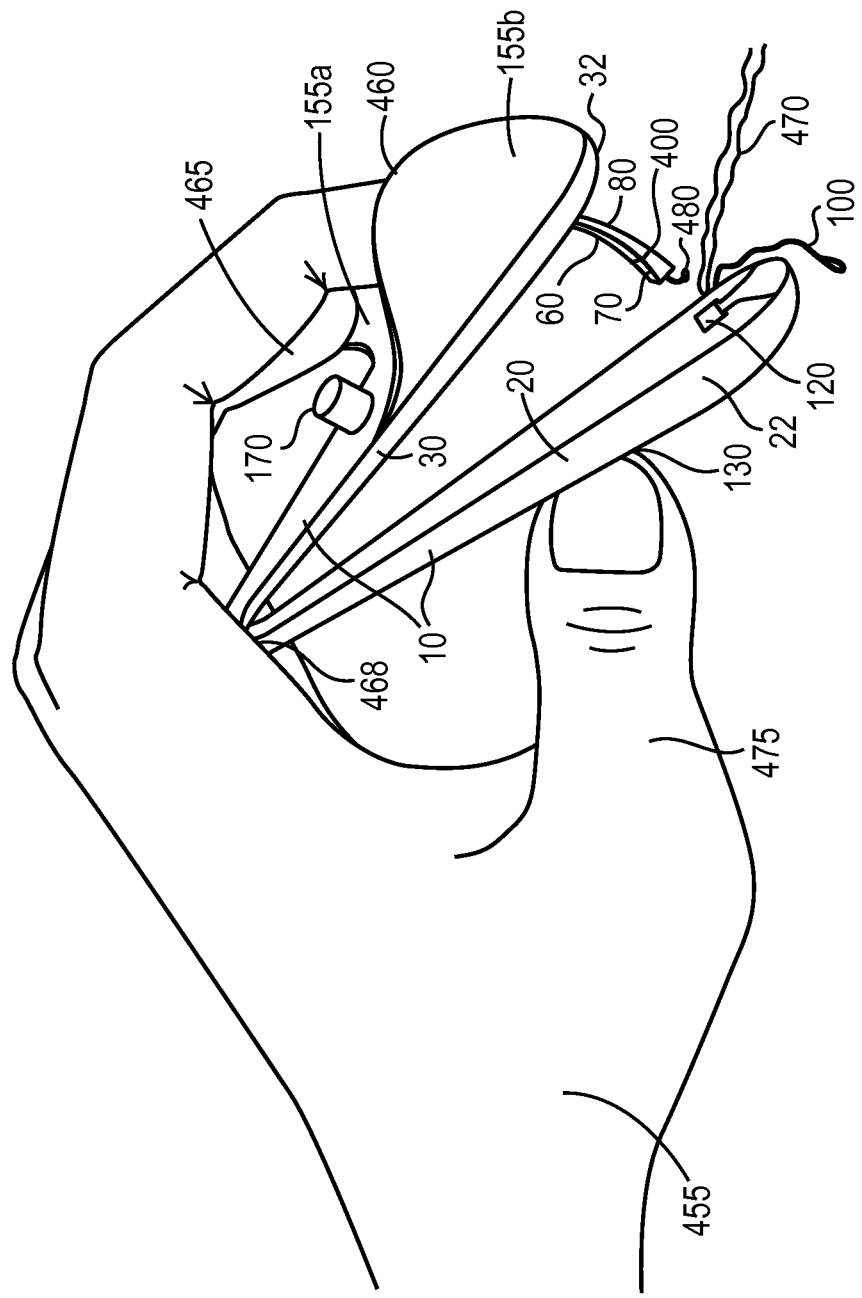

Referring now to FIG. 9B, having guided the pointed end 90 of the suturing needle 60 across the incision, the surgeon then leverages the distal end 22 of the driver arm 20 toward the distal end 32 of the receiver arm 30, and pushes the pointed end 90 into the receiver arm aperture 160 (not shown) until the receiver arm's locking mechanism engages the pointed end indentation 410 (FIG. 8B). The lateral shields 155a and 155b protect the fingers from potential needle sticks by the pointed end 90 of the suturing needle 60. Once the pointed end 90 is secured in the distal end 32 of the receiver arm 30, the thumb 475 presses on the driver arm release button 130 to release the blunt end 70 of the suturing needle 60 from the driver arm's locking mechanism. The needle shaft 80, the blunt end 70 and the attached suturing material 100 are then advanced through the tissue by pulling on the receiver arm 30 through the finger shields 155a and 155b (see FIG. 2C for structural detail).

Figure 9C:
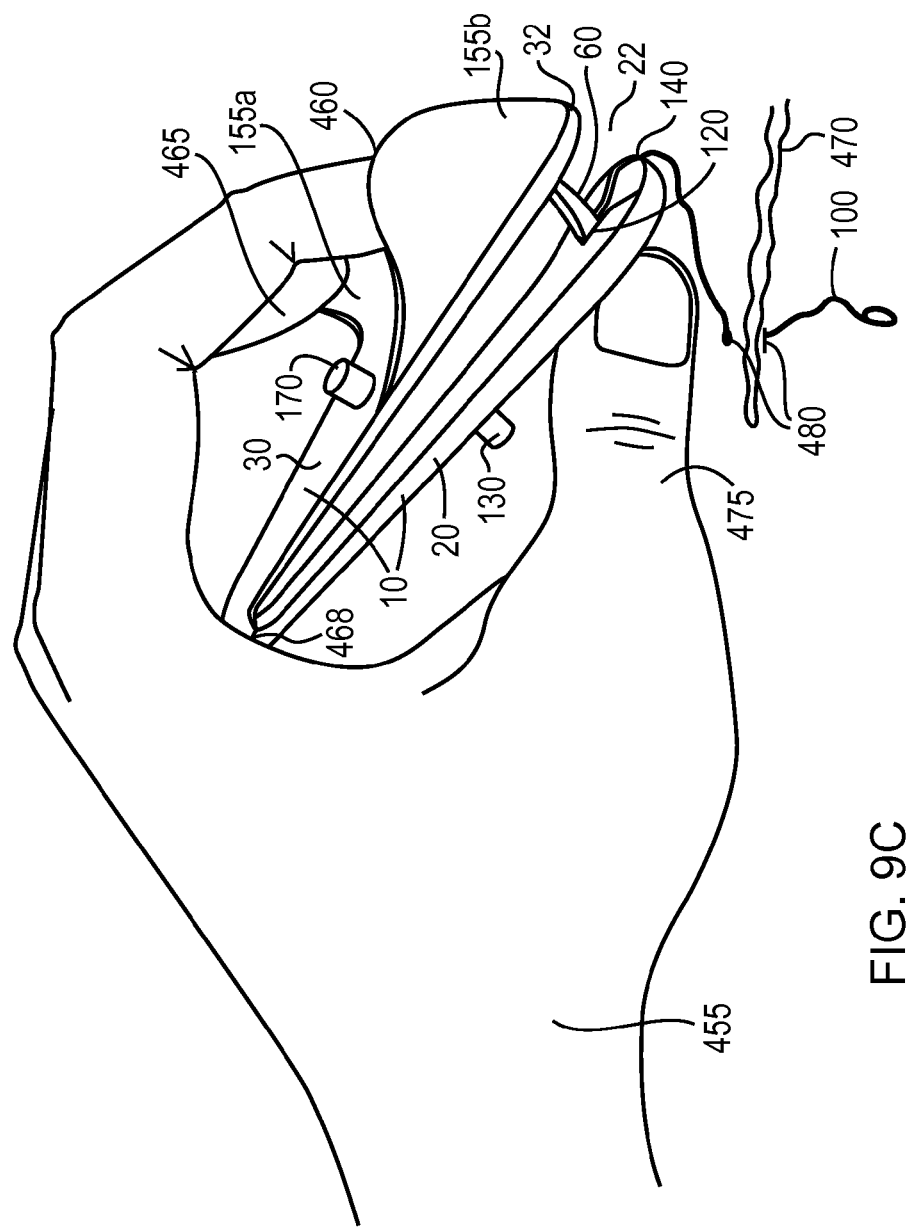

In FIG. 9C, following the position achieved in FIG. 9B, the surgeon removes the thumb 475 away from the driver arm release button 130 and then relays the suture needle 60 from the receiver atm 30 back to the driver arm 20. Accordingly, with the pointed end secured by the receiver arm's locking mechanism, the operator pivots the distal end 32 of the receiver arm 30 about the hinge 468 toward the distal end 22 of the driver arm 20. The blunt end 70 of the suturing needle 60 then passes through the driver arm aperture 120 and is re-secured by the driver arm's locking mechanism (FIG. 7B).

Figure 9D:
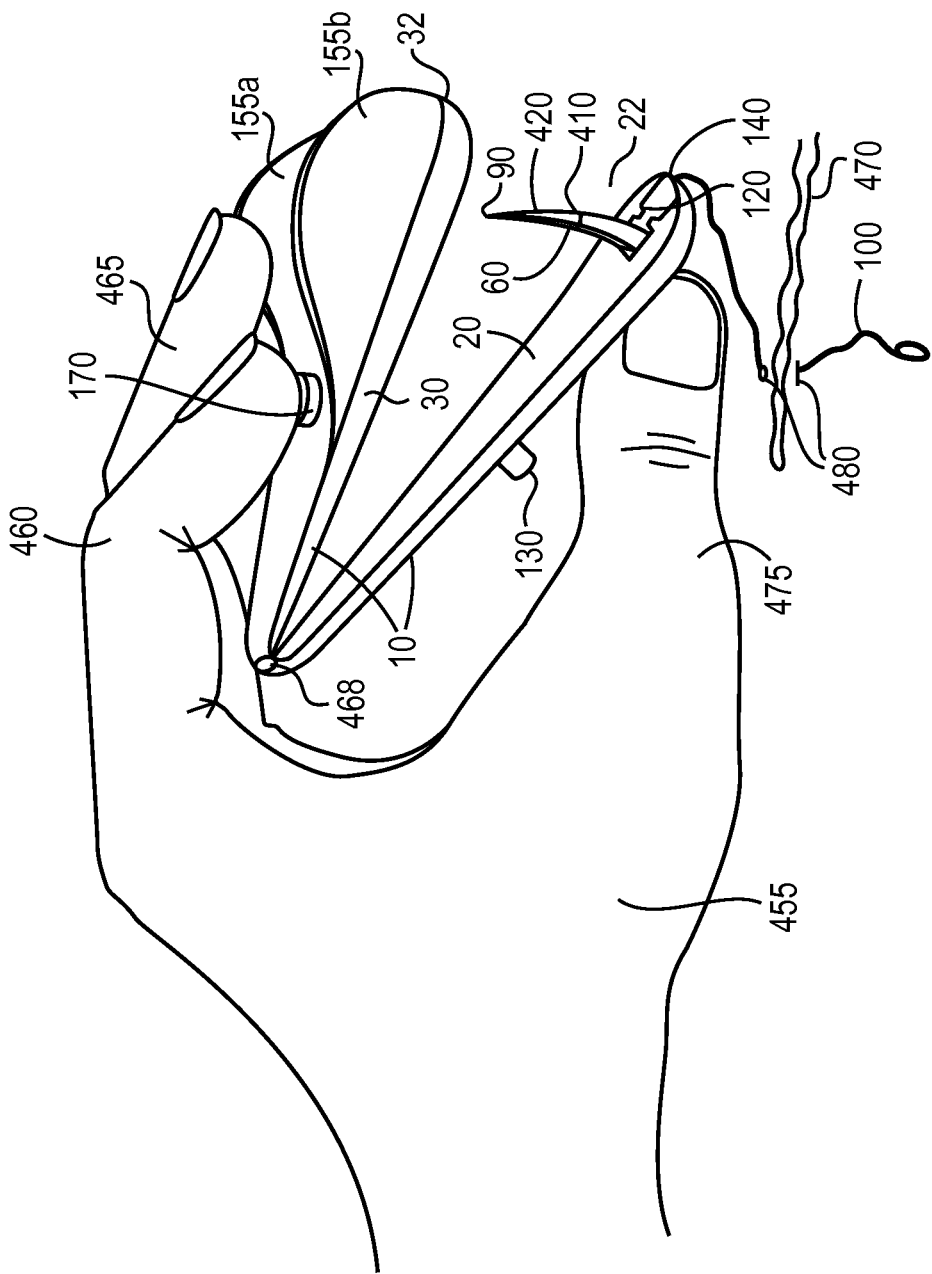

Referring now to FIG. 9D, following the capture of the blunt end 70 by the driver arm 20 depicted in FIG. 9C, the surgeon then presses the index finger 460 on the receiver arm release button 170 to release the pointed end 90 from the receiver arm's locking mechanism. The pointed end 90 of the suturing needle 60 is then free, and the surgeon can repeat the suturing procedure as needed. After completion of the final suture, a surgical knot is tied. In certain embodiments, the spring can be removed and the blunt end 70 and the pointed end 90 of the suturing needle 60 are then securely locked between the driver arm clasp 230 and receiver arm clasp 310 prior to safe disposal.

The disclosure herein also provides for a kit format comprising one or more suturing devices and a packaging unit that preserves sterility of the contents. In some embodiments, the kit may also contain one or more types of suturing needles attached to various types of suturing materials as described herein depending on the intended use. Appropriate instructions for use of the contents including proper suturing instructions are also provided in the kit.

The suturing device of the present invention is designed to assist doctors, embalmers, and surgeons in repairing soft tissue wounds. The suturing device may be used to introduce stitches into many different types of soft tissue, including, but not limited to, skin, muscle, cartilage, fascia, ligaments, gingiva, hollow organs, blood vessels, bowel, surface and interior tissues of the heart or any other soft tissue of the human body that has been severed by injury, incision or surgery.

For this purpose, the suturing device of the present invention can be configured as to length, shape, locking and release mechanism, tip, needle, suture, and size for use in conventional open surgery as well as in minimally invasive surgery (MIS) and in "less-invasive" surgery, such as through natural orifices or through small incisions. Additionally, portions of the arms can be oriented in any preferred direction and either fixed in a particular orientation, or rendered movable in a variety of orientations by an articulation means. In particular, parts for locking the needle, e.g., the clasps or a special housing, can be designed and manufactured as removable parts from the rest of the suturing device and even of a different material. In one embodiment, such removable parts can be made of a relatively inexpensive and disposable material while the rest of the suturing device is made of a more expensive and reusable material. In particular, there can be a removable housing made of disposable materials around the receiver arm clasp—after the operator locks the needle's pointed end securely with the clasp, the operator can remove the housing, with the needle tip enclosed, along with or without the clasp, and safely the needle, allowing the rest of the device to be sterilized for reuse.

The suturing device of the present invention can be useful as an emergency care apparatus to be used to stitch up wound outside a medical facility, e.g., during a field trip, hiking, or on the battlefield. The simplicity of the device lends itself to be useable by people with relatively little or no medical training, and can be easily carried on a trip. For that purpose, the invention envisions one embodiment IP be an emergency care kit with the suturing device and other conventional components of an emergency care kit such as bandage, and antiseptics.

While this invention has been particularly shown and described with references to preferred embodiments thereof, it will be understood by those skilled in the art that various changes in form and details may be made therein without departing from the intended scope of the invention encompassed by the following appended claims. All printed publications cited herein are incorporated by reference as applicable under relevant patent laws.

The invention claimed is:

1. A suturing device comprising:
   a) a driver arm comprising a distal end, a proximal end and a driver clasp, said driver clasp being disposed near said distal end of said driver arm and configured to reversibly secure a suturing needle to said driver arm, wherein said driver clasp comprises:
      i) a first arm comprising a distal end, a proximal end, an inner face and an outer face;
      ii) a second arm comprising a distal end, a proximal end, an inner face and an outer face,
         wherein said first arm and said second arm are moveable between an open position and a closed position, said proximal end of said first arm and said proximal end of said second arm are joined to each other such that said first arm and said second arm are biased toward said closed position, and, in said closed position, juxtaposition of said inner face of said first arm and said inner face of said second arm defines a first aperture oriented for loading a needle and a second aperture; and
      iii) a driver release button, configured to move said first arm and said second arm into an open position after insertion of said driver release button into said second aperture;
   b) a receiver arm comprising a distal end, a proximal end, and a receiver clasp, said receiver clasp being disposed near said distal end of said receiver arm and configured to reversibly secure the suturing needle to said receiver arm; and
   c) a hinge located at both proximal ends of said driver arm and said receiver arm thereby connecting the two, said hinge being configured to allow said distal ends of said driver arm and said receiver arm to converge and separate through rotation about said hinge while keeping said proximal ends of both arms affixed to each other.

2. The suturing device of claim 1, wherein said hinge is configured to confine the rotation of said driver arm and said receiver arm to a single plane.

3. The suturing device of claim 1, wherein said driver clasp and said receiver clasp are disposed directly opposite each other when converged.

4. The suturing device of claim 1, wherein said receiver arm further comprises an aperture to receive and enclose a pointed end of the suturing needle.

5. The suturing device of claim 4, wherein said receiver arm further comprises a finger shield around said aperture and structurally distinct from any part of said receiver arm designed to receive and enclose the suturing needle, said finger shield configured to provide shielding from potential needle sticks in addition to any protection provided by the rest of said receiver arm.

6. The suturing device of claim 1, wherein the receiver arm further comprises a structure for engaging a finger such that said receiver arm can be pulled.

7. The suturing device of claim 1, further comprising a spring disposed between said driver arm and said receiver arm, wherein said spring is biased to separate said driver arm from said receiver arm.

8. The suturing device of claim 1, wherein said driver arm and said receiver arm are sized to be held in a single hand and configured to be operated entirely by that hand.

9. The suturing device of claim 8, wherein neither said driver arm nor said receiver arm is longer than 10 cm.

10. The suturing device of claim 1, wherein both said driver arm and said receiver arm are between 10 cm and 30 cm.

11. The suturing device of claim 1, wherein both said driver arm and said receiver arm are longer than 30 cm.

12. The suturing device of claim 1, wherein said inner faces of said first and second arms of said driver clasp comprise additional texture or an adhesive substance for strengthened gripping power.

13. A suturing device comprising:
   (1) a driver arm comprising a distal end, a proximal end and a driver clasp, said driver clasp being disposed near said distal end of said driver arm and configured to reversibly secure a suturing needle to said driver arm;
   (2) a receiver arm comprising a distal end, a proximal end, and a receiver clasp, said receiver clasp being disposed near said distal end of said receiver arm and configured to reversibly secure the suturing needle to said receiver arm, wherein said receiver clasp comprises:
      (a) a first arm comprising a distal end, a proximal end, an inner face and an outer face; and
      (b) a second arm comprising a distal end, a proximal end, an inner face and an outer face,
      wherein said first arm and said second arm are moveable between an open position and a closed position, said proximal end of said first arm and said proximal end of said second arm are joined to each other such that said first arm and said second arm are biased toward said closed position, and wherein, in said closed position, juxtaposition of said inner face of said first arm and said inner face of said second arm defines one or more apertures; and
   (3) a hinge connecting both proximal ends of said driver arm and said receiver arm, said hinge being configured to allow said distal ends of said driver arm and said receiver arm to converge and separate through rotation about said hinge.

14. The suturing device of claim 13, wherein said juxtaposition defines a first aperture, said first aperture having a contour with at least three sides.

15. The suturing device of claim 14, wherein said contour is triangular.

16. The suturing device of claim 14, wherein said receiver clasp further comprises a receiver release button, said receiver release button being configured to move said first arm and said second arm into an open position after insertion of said receiver release button into a second aperture also defined by said juxtaposition and adjacent to said first aperture.

17. The suturing device of claim 13, wherein said inner faces of said first and second arms of said receiver clasp comprise additional texture or an adhesive substance for strengthened gripping power.

18. A suturing device comprising:
 a) (1) a driver arm comprising a distal end, a proximal end and a driver clasp, said driver clasp being disposed near said distal end of said driver arm and configured to reversibly secure a suturing needle to said driver arm, wherein said driver clasp comprises:
  i) a first arm comprising a distal end, a proximal end, an inner face and an outer face;
  ii) a second arm comprising a distal end, a proximal end, an inner face and an outer face,
   wherein said first arm and said second arm are moveable between an open position and a closed position, said proximal end of said first arm and said proximal end of said second arm are joined to each other such that said first arm and said second arm are biased toward said closed position, and, in said closed position, juxtaposition of said inner face of said first arm and said inner face of said second arm defines one or more apertures comprising a first aperture having a rectangular contour and oriented for loading a needle; and
 (2) a receiver arm comprising a distal end, a proximal end, and a receiver clasp, said receiver clasp being disposed near said distal end of said receiver arm and configured to reversibly secure the suturing needle to said receiver arm,
 (3) a hinge connecting both proximal ends of said driver arm and said receiver arm, said hinge being configured to allow said distal ends of said driver arm and said receiver arm to converge and separate through rotation about said hinge.

* * * * *